United States Patent
Boone

(10) Patent No.: US 7,074,584 B2
(45) Date of Patent: Jul. 11, 2006

(54) YEAST ARRAYS, METHODS OF MAKING SUCH ARRAYS, AND METHODS OF ANALYZING SUCH ARRAYS

(76) Inventor: Charles Boone, 254 Glenrose Avenue, Toronto, Ontario (CA) M4T IK9

( * ) Notice: Subject to any disclaimer, the term of this patent is extended or adjusted under 35 U.S.C. 154(b) by 279 days.

(21) Appl. No.: 10/219,682

(22) Filed: Aug. 15, 2002

(65) Prior Publication Data

US 2003/0099925 A1 May 29, 2003

Related U.S. Application Data

(63) Continuation-in-part of application No. 09/930,593, filed on Aug. 15, 2001, now abandoned.

(51) Int. Cl.
*C12Q 1/02* (2006.01)
*C12N 1/14* (2006.01)
*C12N 1/16* (2006.01)

(52) U.S. Cl. .................. 435/29; 435/254.2; 435/255.1; 435/256.6; 435/454; 435/471

(58) Field of Classification Search .................. 435/29, 435/254.2, 255.1, 256.8, 454
See application file for complete search history.

(56) References Cited

U.S. PATENT DOCUMENTS

2004/0121324 A1* 6/2004 Brenner et al. ................. 435/6

OTHER PUBLICATIONS

Brachmann, et al. (1998). *Yeast* 14: 115-132.
Goffeau, et al. (1996). *Science* 274: 546, 563-567.
Hirsch, et al. (1991). *Genes Development* 5:467-474.
Ho, et al. (2002). *Nature* 415:180-183.
McCusker, et al. (1994). *Genetics* 136: 1261-1269.
Racki, et al. (2000). *Embo J.* 19:4524-4532.
Shoemaker, et al. (1996). *Nat. Genet.* 14: 450-456.
Steinmetz, et al. (2002). *Nature* 416: 326-330.
Sutton, et al. (1991). *Mol. Cell. Biol.* 11:2133-2148.
Tong, et al. (2001). *Science* 294: 2364-2368.
Uesono, et al. (1997). *J. Biol. Chem.* 272:16103-16109.
Winzeler, et al. (1999). *Science* 285: 901-906.
Yang, et al. (1999). *J. Biol. Chem.* 274: 36052-36057.
Winzeler and Davis (1997). *Curr. Opin. Genet. Dev.* 7: 771-776.
Uetz, et al. (2000). *Nature* 403: 623-627.
Roberts, et al. (2000). *Science* 287: 873-880.
Ross-MacDonald, et al. (1999). *Nature* 402; 413-418.
Rao-Naik, et al. (1998). *J. Biol. Chem.* 273: 34976-34982.
Smith, et al. (1996). *Science* 274: 2069-2074.
Guarente (1993). *Trends Genet.* 9: 362-366.
Bender and Pringle (1991). *Mol Cell Biol.* 11: 1295-1305.
Costigan, et al. (1992). *Mol. cell Biol.* 12: 1162-1178.
Holtzman, et al. (1993). *J. Cell. Biol.* 122: 635-644.
Igual, et al. (1996). *EMBO J.* 15: 5001-5013.
Kroll, et al. (1996). *Genetics.* 143: 95-102.
Dimister-Denk, et al. (1999). *J. Lipid Res.* 40: 850-860.

\* cited by examiner

*Primary Examiner*—David Guzo
*Assistant Examiner*—Daniel M. Sullivan
(74) *Attorney, Agent, or Firm*—Ivor R. Elrifi; Naomi S. Biswas; Mintz Levin

(57) ABSTRACT

This patent describes a novel method of detecting genetic interactions in yeast. This method can also be used to screen for function of biological effectors on yeast. The method encompasses crossing yeast strains with genetic alterations to acquire double mutants. The phenotypes of these double mutants are then checked to detect genetic interactions between the double mutants. This method can be used to assign function to yeast genes and their viral, prokaryotic, and eukaryotic homologs, and aptamers. It can also be used to study yeast two hybrid interactions and to find genes that regulate certain yeast promoters.

36 Claims, 8 Drawing Sheets

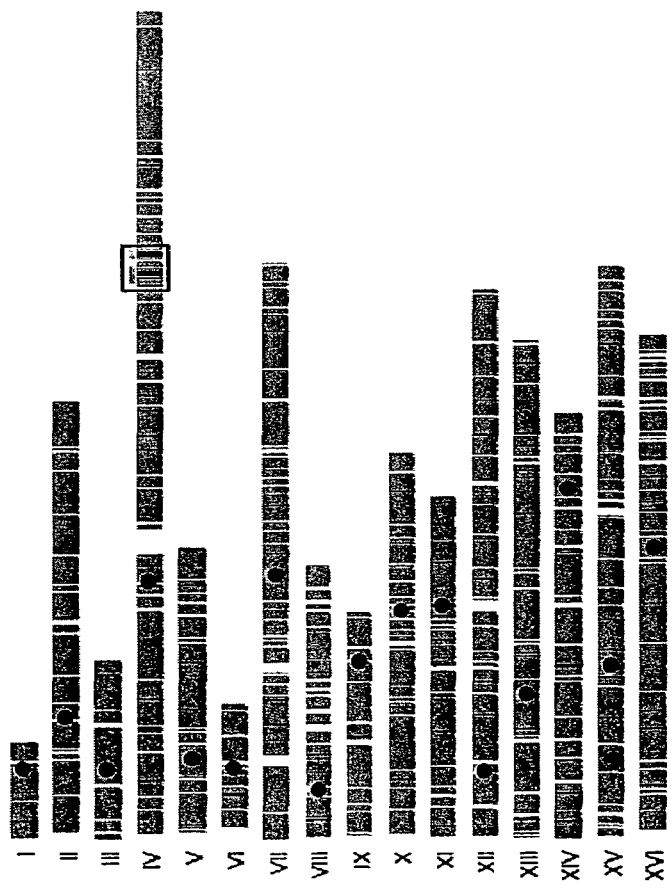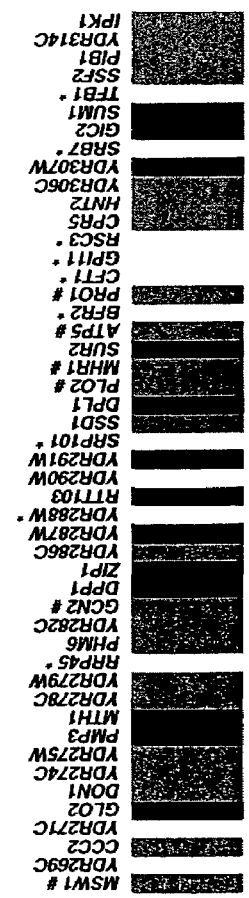
Figure 6

YEAST ARRAYS, METHODS OF MAKING SUCH ARRAYS, AND METHODS OF ANALYZING SUCH ARRAYS

RELATED APPLICATION

This application is a continuation-in-part of U.S. Ser. No. 09/930,593, filed Aug. 15, 2001, now abandoned, which is incorporated by reference in its entirety.

FIELD OF THE INVENTION

The present invention relates generally to genomics and proteomics. More specifically, it relates to high density output arrays of multiple yeast strains, methods of making the high density output arrays, methods of using the high density output arrays for functional analysis of genetic and protein-protein interactions, and methods of mapping genetic mutations using the arrays.

BACKGROUND OF THE INVENTION

One of the major goals of the emerging field of proteomics is the establishment of relationships between protein function and particular diseases. Proteomic technologies are used to try to identify important genes and their related proteins implicated in diseases and their treatments and to understand the role these genes and their related proteins play in the onset and progression of disease. A major proteomics challenge is to determine the set of proteins expressed in the cell and the interactions between such proteins, which in turn define the functional pathways of the cell. If a given pathway is linked to a disease, then the proteins within the pathway or a functionally related pathway may represent drug targets for treatment of the disease.

Accordingly, there is a need in the art for functional proteomics technologies which provide valuable functional information about genes encoding proteins with previously unknown roles. Yeast based proteomics represents one such technology. Functional genomics and proteomics strategies involving large-scale construction of defined mutants have created the potential for the systematic mapping of genetic interactions on a genome-wide scale. In addition to the recent sequencing of the human genome, the genomes of other, simpler, organisms have been completely sequenced, including that of the budding yeast *Saccharomyces cerevesiae*. For *S. cerevisiae*, deletion mutations have been constructed for all 6,200 suspected genes, identifying a set of approximately 1200 essential yeast genes and approximately 5,000 nonessential genes, resulting in approximately 5000 viable haploid gene deletion mutants. With genome sequence in hand, the monumental challenge is to understand the roles of the approximately 6,200 predicted yeast gene products. The scope of the challenge is immense. Approximately one-third of all predicted yeast genes are classified as coding for proteins of unknown function [*Saccharomyces* Genome Database (http://genome-www.stanford.edu/*Saccharomyces*/)]. Further, among a test pool of 558 homozygous deletion strains, over 60% had no observable growth defect after 60 generations. Simple extrapolation to more complex genomes suggests that the absence of obvious functions for a large fraction of encoded proteins will quickly become an enormous problem in biology.

There is a need, therefore, for proteomics technologies which can assess the previously unknown functions of proteins. The phenotypic analysis of the set of viable deletion strains within certain species of yeast represents a major challenge because the role of many genes will only be manifest under very specialized growth conditions. To address this problem, the present invention provides a high throughput method for the construction of yeast double-mutants that enables the phenotype associated with a specific mutation to be examined systematically within the context of thousands of different gene deletion backgrounds. A comprehensive application of this method will identify the precise genetic conditions under which each yeast gene is critical for fitness of the organism and may reveal a conserved network of genetic interactions linking fundamental processes and pathways of eukaryotic cells. Because many non-essential yeast genes have mammalian homologues systematic synthetic lethal analysis on yeast will provide crucial insights into the gene function problem in all eukaryotes. Such synthetic lethal analysis can be performed on the yeast arrays of the present invention. The high density yeast output arrays and the methods of analyzing such arrays of the present invention therefore fulfill a need in the art by providing simple and efficient methods for large-scale, high throughput analysis of genetic and protein-protein interactions.

SUMMARY OF THE INVENTION

The invention is directed to compositions and methods for performing large-scale analysis of genetic and protein interactions.

In one embodiment of the invention a high-density output array of multiple resulting yeast strains is constructed. Each resulting yeast strain in the output array contains at least one resulting genetic alteration different from the genetic alterations in the other resulting yeast strains in the output array.

The resulting yeast strains in the output array are mating products of at least two input arrays. At least one of the input arrays comprises multiple starting strains of yeast, each carrying at least one genetic alteration, with the genetic alteration being different in each starting yeast strain. The starting and resulting yeast strains are selected from any yeast strain that has two mating types and is capable of mating and meiotic and mitotic reproduction. Examples of species that have such strains are *Saccharomyces cerevesiae* and *Schizosaccharomyces pombe*.

The input and output arrays are arranged on plates, with between about 96 and about 6144 yeast colonies on one plate, and much higher densities, over 10-fold higher, can be achieved if individual colonies are pooled. The resulting strains in the output array are double mutants. Two different types of output arrays are created, one in which the phenotypes associated with mutations (genetic alterations) are examined within a diploid cell formed by mating the strains on the input arrays and another in which mutations are examined within the context of a haploid cell following sporulation of the diploids. The two mutations can involve a mutation of two different endogenous yeast genes. These yeast genes can be non-essential yeast genes. Interactions between deleted genes in the output array can be discerned when the combination of genes leads to either a synthetic lethal double mutant or a synthetic sick double mutant, i.e. where the double mutant grows more slowly than either of the single mutants on the input arrays. The entire output arrays can comprise between about 1,000 and about 25 million resulting strains of yeast, or between about 1 million and about 25 million resulting yeast strains.

The input array contains starting yeast strains with starting genetic alterations in at least one starting yeast strain. The genetic alterations can be of any of the following type:

(i) an alteration in the DNA encoding the gene such as a deletion or mutation of an endogenous essential or non-essential yeast gene; (ii) trans-dominant genetic agents such as genes coding for nucleic acid or peptide aptamers, dominant-negative proteins, antibodies, small molecules, natural products, ribozymes, enzymes, RNAi, and antisense RNA or DNA; (iii) protein and RNA expression vectors of a heterologous gene from a viral, prokaryotic, or eukaryotic genome, wherein the genes can either be wild type, mutated or fragmented (e.g. coding for a protein domain); (iv) a protein-protein interaction detection system, including expression plasmids coding for a two-hybrid interaction and reporter that registers the interaction, the Ras recruitment system, the split-ubiquitin system, and various other protein fragment complementation systems (e.g. DHR); and (v) a reporter whose expression reflects a change in cellular state such as the activation or the inhibition of a pathway(s). The genetic alterations can be integrated into the yeast genome or propagated on autonomously replicating plasmids.

The aptamer can be either a peptide aptamer or a nucleic acid aptamer. It can either inhibit or enhance expression of genes, protein interactions, or the activity of a protein or any other cellular component.

The heterologous gene can be a human gene that can be a single nucleotide polymorphism of another human gene.

In another embodiment of the invention, a high-density output array of resulting multiple yeast strains, where each resulting yeast strain carries at least one resulting genetic alteration, and the resulting genetic alterations are different in each yeast strain, is constructed through the method disclosed below. Multiple starting yeast strains are generated, each strain carrying a starting genetic alterations. Sets of two starting yeast strains, each of the two sets containing a different starting genetic alteration; are then mated. The mated strains are then made to undergo sporulation, resulting in haploid spore progeny. A single mating type is then germinated and the haploid spore progeny is cultured using selective growth criteria. Multiple haploid yeast strains which carry a resulting genetic alteration which is a combination of at least two starting genetic alterations are selected for through this process. The genetically altered yeast strains are then arrayed in a high-density format on an output array.

The strains, plates, and genetic alterations used in this embodiment are similar to the previous embodiment. The output array described in this embodiment could also be used to perform synthetic lethal analysis as described in the previous embodiment.

Yet another embodiment of the invention is a method for conducting small molecule screening of yeast colonies using a high-density input array of multiple starting yeast strains. The method is carried out by generating an input array containing multiple starting yeast strains as described above. Then exposing this array to at least one biological effector, and detecting change in phenotype in the starting strains in response to the effector. The effector can be a small molecule or any other biological effector. The input array and genetic alterations can be the same array described in previous embodiments.

Yet another embodiment of the invention is a method for conducting synthetic lethal analysis of yeast colonies by producing an input array of starting strains, and crossing the starting strains in that array with other starting strains or another input array. Then the diploid resultant strains are studied for changes in phenotype due to the combination of different genetic or chemical alterations.

The input arrays are constructed as detailed in the embodiment above. The genetic alterations can be the same as the ones in the embodiments above. Chemical alterations can include biological effectors such as the ones described in the previous embodiment.

Yet another embodiment of the invention is a method to perform synthetic lethal analysis of yeast colonies of multiple yeast strains using DNA bar coding. In this method, starting strains are constructed as described above, but not placed into arrays. Each of the genetic alterations has a distinct DNA tag associated with it. This tag can be a 20 nucleotide long DNA sequence associated with a certain genetic alteration. These starting strains are mated with other starting strains of a different mating type, which generates the first output strain set, and then stimulated to undergo sporulation, which allows for selected growth of haploid spore progeny that possess of both genetic alterations and generates the second output strain set. The resulting output strains are then studied and isolated through their genetic tags, dispensing with the need to array each strain. The genetic alterations used in this embodiment can be the same alterations used in the previous embodiments.

A still further embodiment of the invention is a method for high resolution mapping of a gene or a plurality of genes in an organism such as yeast, which includes crossing a query yeast strain carrying at least two genetic alterations systematically with a plurality of resulting multiple yeast strains, where each resulting yeast strain carries at least two resulting genetic alterations, and where the resulting genetic alterations are different in each yeast strain; observing an epistatic phenotype in one or more of the systematic crossings; and determining the position of the at least two genetic alterations in the query strain relative to the position of the at least two resulting genetic alterations in each of the plurality of multiple yeast strains based on the observation, thus mapping one or more genes. The plurality of multiple yeast strains may be in an array.

BRIEF DESCRIPTION OF THE DRAWINGS

FIG. 6A shows SGA analysis with gene deletions of Cbk1 pathway components and revealed dispersed synthetic interactions as well as an apparent set of colinear synthetic interactions on chromosome IV. Starting strains deleted for CBK1, MOB2, HYM1, KIC1, and TAO3 were subjected to SGA analysis versus a near complete set of ~4700 kanR-marked, viable haploid deletion strains. Gene deletions included in this set are represented as gray lines and cover nearly the whole genome from chromosome I to XVI. Gene deletions consistently exhibiting synthetic interactions with Cbk1 pathway deletions, found in at least 4 out of 5 of the screens, are represented as black lines and were found scattered throughout the genome. Centromeres are represented as a filled black circle. A set of genetic interactions in a ~90 kb region of chromosome IV (boxed) was identified as statistically significant by an algorithm that measures the density of synthetic interactions over a sliding window of 11 genes. The boxed region localizes the W303-specific suppressor of Cbk1 pathway deletions.

FIG. 6B shows a magnification of the boxed ~90 kb region of chromosome IV. Genes are represented as in (6A). Essential genes are marked with * and are not represented by haploid deletion mutants. Deletion strains that are consistently slow growing in SGA analysis and beyond the sensitivity of the assay, are marked with # next to the corresponding gene.

FIG. 6 presents the cumulative data from SGA analysis carried out against deletions in all five components of the Cbk1 signaling pathway, the synthetic interactions listed in FIG. 6 differ somewhat from those observed in this single screen versus tao3Δ:: URA3.

DETAILED DESCRIPTION

Figure 1:
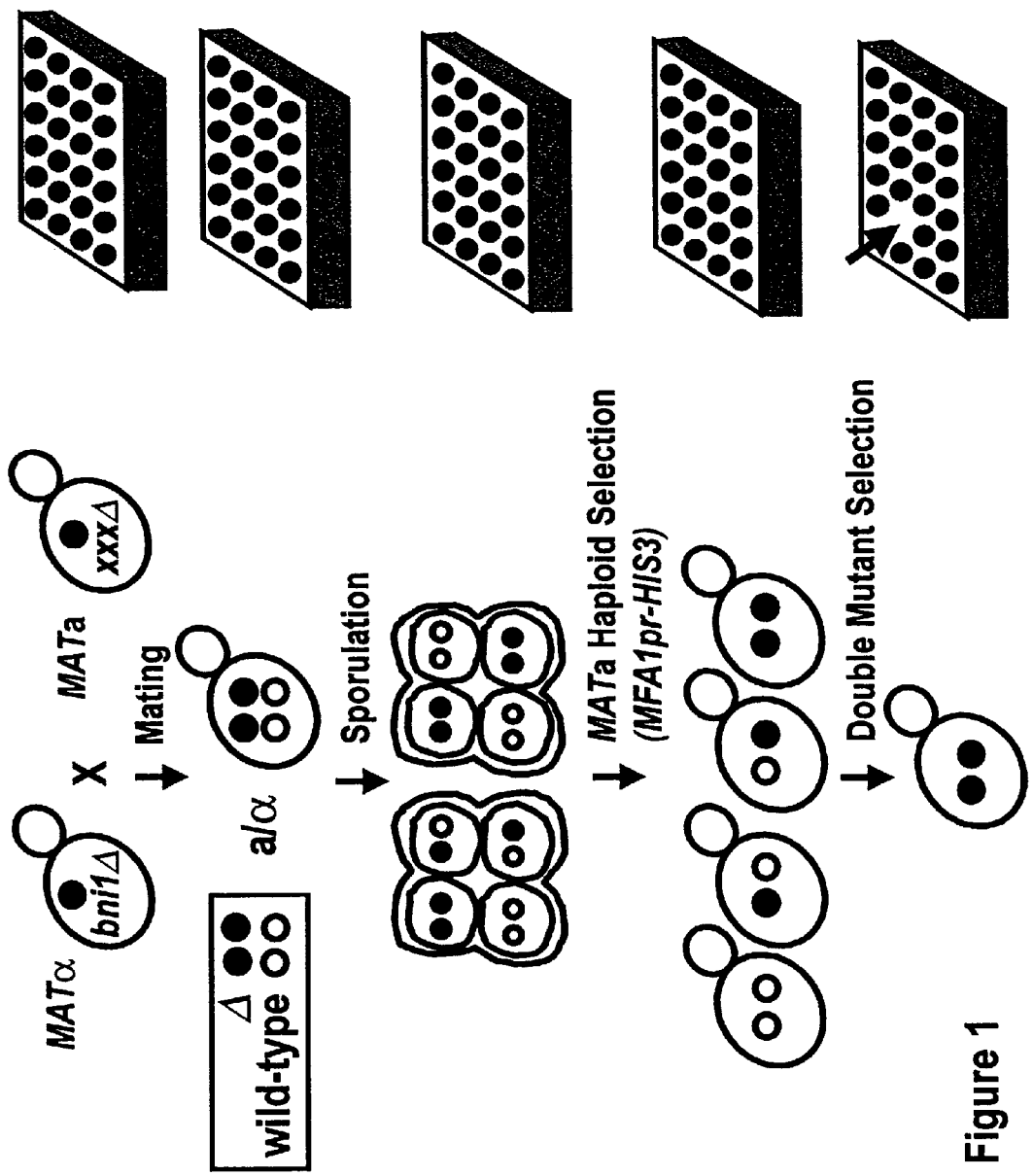
FIG. 1 illustrates the series of replica pinning procedures in which mating and meiotic recombination are used to generate haploid double mutants.

The present invention is directed to high-density output arrays of multiple yeast strains, methods for constructing such arrays, and methods of using such arrays to conduct large-scale high throughput analysis of genetic and protein-protein interactions. The present invention provides a systematic and efficient method for constructing arrays of yeast strains carrying multiple genetic alterations. This invention enables a large-scale analysis of genetic and protein-protein interactions, provides a method for validating potential drug targets and for generating whole cell screens for compounds that perturb the function of these targets.

More specifically, the present invention provides compositions and methods that will enable the systematic and automated construction of arrays of yeast strains containing multiple mutations in a high-throughput manner. For example, the present invention could be used to generate a high density output array of approximately 25 million double mutant yeast strains, through crosses of input arrays involving approximately 5,000 viable haploid deletion mutants. The resulting output arrays can be used for large-scale analysis of genetic and protein interaction networks by identifying the complete set of synthetic lethal double mutant combinations for a model eukaryotic cell.

The invention is directed to a variety of high-density yeast arrays, methods of making such arrays, and methods of using such arrays. The arrays include both input and output arrays. Input arrays are those arrays used to generate output arrays. Input arrays are arrays of multiple yeast strains, with each yeast strain containing at least one genetic alteration. These input arrays are crossed with either other starting yeast strains that contain at least one genetic alteration, or other input arrays to produce output arrays. Output arrays are therefore generated by crossing starting yeast strains from input arrays. The starting yeast strains each have at least one genetic alteration. Crossing of the starting yeast strains containing at least one genetic alteration results in strains of the output arrays containing at least two genetic alterations. These genetic alterations present in both the input and output arrays can include, but are not limited to, members of the group consisting of an aptamer, a system for detecting protein-protein interactions, including a yeast two-hybrid system, expression of a heterologous gene from a viral, prokaryotic, or eukaryotic genome with the heterologous gene either having or not having a yeast homolog, transformation with a promoter operably linked to a reference gene, wherein the reference gene can be a reporter gene, mutation or deletion of an endogenous essential or non-essential yeast gene, or the addition of other dominant agents which can perturb any cellular function, including genes coding for dominant negative proteins, antibodies, small molecules, natural products, ribozymes, RNAi, and antisense RNA or DNA.

As used herein, an input array is a grouping of a multitude of starting yeast strains located together on a solid support. In one embodiment, the solid support is a plate. In a preferred embodiment, there are between about 96 and 6144 colonies on one plate, preferably the array would be constructed at the highest density physically possible, which is limited by cell size and the number of genetically different strains that can be pooled and manipulated as one element of the array. The starting strains in the input array are selected from yeast species that has two mating types and is capable of meiotic and mitotic reproduction. In preferred embodiments, the starting yeast strains can be from either the *Saccharomyces cerevesiae* species or the *Schizosaccharomyces pombe* species.

As discussed above, the genome of *S. cerevisiae* has been completely sequenced, and approximately 6,200 genes have been located. The international *S. cerevisiae* deletion consortium has constructed mutants corresponding to all of the approximately 6,200 suspected genes within the *S. cerevisiae* genome, with each mutant being a strain of yeast containing a deletion of a different endogenous yeast gene. Tetrad analysis has revealed that approximately 15% of these deletion mutations define genes essential for the viability of haploid cells, also referred to as "essential genes". Thus, the deletion consortium identified approximately 1,200 essential genes and approximately 5,000 nonessential genes.

The set of approximately 1,200 essential genes does not define the minimal set of genes required for life because many genes that are individually dispensable are not simultaneously dispensable. Synthetic genetic interactions are usually identified when a specific mutant is screened for second-site mutations that either suppress or enhance the original phenotype. In particular, two genes show a "synthetically lethal" interaction if they are associated with viability as single mutations but combine to cause a lethal double-mutant phenotype. This phenotype in which a particular gene is only required for cell viability when another gene is also deleted is called a "synthetic lethality defect". Similarly, the deletion of some genes results in a more severe growth defect only when combined with the deletion of another gene, a phenotype referred to herein as a "synthetic fitness defect". Because both synthetic lethal defects and synthetic fitness defects represent genetic interactions, the reference herein to synthetic lethal interactions or relationships also applies to synthetic fitness interactions.

Many synthetic lethal relationships appear to be specific, occurring for genes acting on a single biochemical pathway. They also occur, however, for genes within two distinct pathways if one process functionally compensates for defects in the other or if the two processes are functionally related. Genetic screens for synthetic lethal interactions traditionally involve three labor-intensive steps: (1) mutagenesis of a strain that carries a mutation in a "query" gene of interest; (2) isolation of mutants whose growth is dependent upon expression of the query gene; and (3) cloning of the synthetically lethal gene by complementation with a plasmid-born genomic library. Synthetic lethal screens have been applied successfully to identify genes involved in cell polarity, secretion, DNA repair, and numerous other processes. On average, three to four different interactions were identified per screen, but very few of the published screens approach saturation.

With a collection of defined mutations, synthetic lethal interactions can also be identified through systematic construction and analysis of double-mutants. The identification of synthetic lethal/fitness double-mutant combinations often indicates significant in vivo interactions between gene products and serves as a key starting point for targeted biochemical or cell biological experiments. Indeed, a synthetic lethal/fitness mutant combination is often observed for genes that impinge on the same essential cellular function. As described above, because the genome of *S. cerevesiae* is sequenced and most of the essential and non-essential genes are determined, yeast arrays crossing strains with deletions or mutations of non-essential genes can be generated in order to study the effects of double mutations. Accordingly,

*S. cerevesiae* is an organism which works well in the high-density output yeast arrays of the present invention.

Additionally, the same methods described herein for the *S. cerevisiae* genome wide deletion set can be applied to other yeasts once analogous deletion sets are constructed. In particular, the fission yeast *Schizosaccharomyces pombe* has proven an invaluable complementary organism to budding yeast for cell and molecular genetic analysis. The completion of the fission yeast genome presents an enormous opportunity for comparative biology between the two distantly related yeasts. Within the next several years, a complete gene deletion set will certainly be constructed by the *S. pombe* community, and would be easily amenable to the systematic synthetic lethal analysis using the large-scale genetic and protein interaction analysis methods of the present invention. Any other fungal species that has two mating types can also be used with the present invention.

As stated above, the input array of the present invention contains a multitude of starting yeast strains. The array could contain, for example, about 5000 different yeast strains, each of which contains a different gene deletion. Such an input array could be crossed with a second input array, which also contains about 5000 different yeast strains, each of which also contains a gene deletion. This type of output array containing approximately 25 million (5,000×5,000) different yeast strains is described in detail in Example 5. Or, in another embodiment, an input array of about 5000 different yeast strains could be crossed with only one starting strain. Examples of these types of crosses are described in detail in Example 6. In yet another embodiment, more specific input arrays can be crossed with specific deletion mutants, as illustrated in Examples 7–10. The possibilities of different crosses between a first input array and a second input array or between a first input array and a starting strain are quite numerous, and will be discussed in more detail below.

In one embodiment of the invention, a first input array contains yeast strains, which are modified so that they contain at least one non-lethal genetic alteration. The first input array is then crossed with either another yeast starting strain or another input array, which also contains at least one genetic alteration, to form an output array containing double mutants. Double mutants as used herein means yeast strains which contain two genetic alterations, derived from single mutants each of which contains at least one genetic alteration.

An output array is the product of a cross between either two input arrays or an input array and a starting strain. The input arrays and/or starting strain to be crossed are of different mating type, to allow for selection of the genetic alterations formed after the cross. For high-throughput synthetic lethal analysis with the set of viable yeast gene deletion mutants, the present invention provides a series of replica pinning procedures in which mating and meiotic recombination are used to generate two output arrays, one composed of diploid cells carrying genetic alterations derived from the input arrays and another output array containing haploid meiotic progeny carrying genetic alterations derived from the input arrays (FIG. 1). In this scheme, a query mutation is first introduced into a haploid starting strain, of one mating type, and then crossed to the array of gene deletion mutants of the opposite mating type. A set of diploids that are heterozygous for both mutations represents the first output array that can be analyzed for a phenotype. Sporulation of the diploid cells leads to the formation of double-mutant meiotic progeny and the second output array. The starting strain carries a reporter that allows for selected germination of spores, which ensures that conjugation of meiotic progeny does not complicate the final analysis. Both the query mutation and the gene deletion mutations can be linked to dominant selectable markers, which enables selected growth of double-mutants specifically. The final pinning results in an ordered array of double-mutant strains, whose growth rate is monitored by visual inspection or image analysis of colony size.

The output arrays are generated by performing the following steps. The first step is to generate multiple starting yeasts strains, with each of these starting yeast strains carrying a genetic alteration. These starting yeast strains are then grouped into either two input arrays, or one input array and a particular starting strain. The input arrays are then crossed (mated), and diploid strains result, forming the first output array. The mated diploid strains then undergo sporulation, resulting in haploid strains. A single mating type is germinated. The haploid spore progeny that result from this sporulation are then grown using selective growth criteria. Multiple haploid yeast strains, which grow on the selective media, can then be selected for the presence of genetic alterations that were in the starting strains. These recovered haploid yeast strains can then be arrayed in a high-density format forming the second output array.

output array can contain hundreds, thousands, or millions of resulting yeast strains with genetic alterations. In one embodiment, the output array contains between about 1,000 and 25 million resulting yeast strains, and more preferably between about one and about 25 million resulting yeast strains. Because the output array can be produced in such a high-density format, containing millions of yeast strains, the output array can be used to assign gene function to multiple genes simultaneously. The high-density output array also allows for large-scale analysis of genetic and protein interactions, by analyzing the phenotypes of the resulting strains within the output array.

One type of analysis that can be performed on the high-density output arrays is a synthetic lethal/synthetic fitness analysis. Such an analysis is used to determine the presence or absence of synthetic lethality defects or synthetic fitness defects. Synthetic lethality defect and synthetic fitness defect are phenotypes wherein either cell death or retarded cell growth occurs only when two different genes are deleted at the same time. When a specific gene is required for cell viability under conditions when a different gene is deleted or mutated, this resulting phenotype is termed a "synthetic lethality defect". This phenotype is so named because the two genes deleted together synthetically lead to cell death. Similarly, the deletion of some genes results in a more severe growth defect only when combined with the deletion of another gene, a phenotype referred to as a "synthetic fitness defect". Experience suggests that a fraction of the genes of unknown function in *S. cerevisiae* will not exhibit synthetic lethal interactions with other single deletions. However, this defined subset represents the next logical target for a subsequent round of synthetic lethal screens that would yield genes that are essential only when two other genes are deleted. A slight modification of the selection scheme will allow the synthetic lethal screens to be reiterated. By definition, when taken to the limit, this approach will identify the function of all genes encoded by the yeast genome.

The identification of synthetic lethal/fitness double-mutant combinations often indicates significant functional interactions between gene products or the pathways containing the gene products and serves as a key starting point for targeted biochemical or cell biological experiments. Accordingly, when a first input array is crossed with either a second input array or a starting yeast strain, the phenotypes of the crosses are studied to see if the resulting strain develops a synthetic fitness, or synthetic lethal phenotype, or any other discernible phenotype. In particular, the methods used in this invention include the use of groups of fungal strains that contain genetic alterations. These strains can be crossed in order to study the phenotype of a strain with at least two genetic alterations.

The genetic alterations can be of any of the following types: (i) an alteration in the DNA encoding the gene such as a deletion or mutation of an endogenous essential or non-essential yeast gene; (ii) introduction of trans-dominant genetic agents such as genes coding for peptide or nucleic acid aptamers, dominant-negative proteins, antibodies, small molecules, natural products, nucleic acid aptamers, ribozymes, enzymes, RNAi, and antisense RNA or DNA; (iii) protein and RNA expression vectors of a heterologous gene from a viral, prokaryotic, or eukaryotic genome, wherein the genes can be either wild type, mutated, or fragmented (e.g. coding for a protein domain); (iv) a protein-protein interaction detection system, including expression plasmids coding for a two-hybrid interaction and reporter that registers the interaction, the Ras recruitment system, the split-ubiquitin system, and various other protein fragment complementation systems (e.g. DHR); and (v) a reporter whose expression reflects a change in cellular state such as the activation or the inhibition of a pathway(s). The genetic alterations can be integrated into the yeast genome or propagated on autonomously replicating plasmids.

The input arrays and starting yeast strains which are crossed to produce an output array can contain within them a variety of genetic alterations, which allow for analysis of a variety of different modifications. In one embodiment of the invention, the yeast starting strains in the input arrays have a gene deletion introduced into them as their genetic alteration. This gene deletion could be of an essential, or non-essential gene. Non-essential gene deletions are deletions or mutations of genes that do not produce a lethal phenotype. In *Saccharomyces cerevesiae*, there are approximately 5,000 non-essential genes which, when either deleted or mutated, do not produce a lethal phenotype. Combinations of non-essential genes deletions can produce synthetic lethal or synthetic fitness phenotypes that will reveal how these genes interact, what their function is in yeast i, and what the function of their homologs are in humans or other organisms. Combinations of these genes could also lead to other discernible phenotypes, which could suggest the function of the deleted genes.

Essential genes are genes that when deleted or mutated cause a lethal phenotype. The function of essential genes can be studied by modulating their expression using inducible promoters. Similarly, conditional mutations can be introduced into essential genes allowing the mutant phenotype to be analyzed under defined conditions. For example, temperature sensitive mutations are viable at a permissive temperature and inviable at a restrictive temperature.

In one embodiment of the invention, an input array with a non-essential or essential gene deletion can then be crossed with other starting strains that contain other gene deletions, or any other genetic alteration. Genetic alterations mentioned in regards to this invention may include: non-essential gene deletions; essential gene deletions; aptamers; exogenous genes, either wild type, mutated, or fragmented (e.g. coding for a protein domain); genes coding for ribozymes; enzymes; RNAi, and antisense RNA or DNA; systems for detecting protein-protein interactions such as the yeast two-hybrid system; and reporters whose expression reflects changes in cellular state.

In another embodiment of the invention, yeast-starting strains in the input arrays have aptamers either integrated into their genome or introduced as expression plasmids as their genetic alteration. Aptamers are peptide or nucleic acids that are produced through at least partially randomized pools of nucleic acid or amino acid sequences, that are selected for their ability to bind certain epitopes. Peptide aptamers are defined as affinity agents that consist of constrained combinatorial peptide libraries displayed on the surface of scaffold proteins. Peptide aptamers are trans-dominant agents that interact with gene products.

Ordered arrays of yeast strains expressing peptide or nucleic acid aptamers can substitute for arrays of yeast deletion strains. In this embodiment, starting strains containing gene deletions are crossed to an array of strains expressing peptide or nucleic acid aptamers and haploid meiotic progeny expressing the peptide aptamer and carrying the gene deletion can be selected. The resulting strains that show aptamer-dependent synthetic lethality identify aptamers that inhibit a gene product whose activity is required for viability of the starting gene deletion strain. The array of strains expressing peptide aptamers could also be used to identify dominant inhibitors. In this case, a strain carrying a query mutation would be crossed to an array of strains expressing peptide aptamers and the resultant diploid cells examined directly for a phenotype. Those that show aptamer-dependent synthetic lethality as diploids would identify an aptamer that inhibits a gene which shows a genetic interaction with the heterozygous query mutation.

Aptamers can inhibit the function of gene products by any one of, but not limited to only, the following mechanisms: (i) modulating the affinity of a protein-protein interaction; (ii) modulating the expression of a protein on a transcriptional level; (iii) modulating the expression of a protein on a post-transcriptional level; (iv) modulating the activity of a protein; and (v) modulating the location of a protein. The precise mechanism of action of peptide aptamers can be determined by biochemical and genetic means to ascertain their specific function in the context of their interaction with other genes, and gene products. Strains carrying characterized aptamers can then be crossed with other starting strains that contain peptide aptamers or any other genetic alteration as described above. The phenotypes of these crosses can then be studied to determine if the resulting strains in the output array develop a synthetic fitness, or synthetic lethal phenotype, or any other discernible phenotype.

In another embodiment of the invention, the starting strains would carry a heterologous gene or gene combination with a readout of gene product activity. For example, the starting strain may contain a heterologous gene encoding an enzyme for which there is a biochemical assay for its activity. In another example, the starting strain may carry a yeast two-hybrid protein-protein interaction system or some other protein-protein interaction detection system such as the Ras recruitment system, the split-ubiquitin system and various other protein fragment complementation systems (e.g. DHR), which can be crossed to yeast within the input array that contain other yeast two-hybrid interaction systems, or any other genetic alteration. The genetic alterations in the other starting strain could be any of the ones defined above or any other genetic alterations. The phenotypes of these crosses can be studied to determine if any of the resulting strains within the output array perturb the two-hybrid interaction. For example, if an input starting strain carries a set of genes that allow for the formation and detection of a two-hybrid interaction and the strains within the input array carry yeast gene deletions, then the output array would allow for the identification of deletions that perturb the two-hybrid interaction; or if the strains within the input array carry peptides aptamers, then this system can be used to identify dominant inhibitory peptide aptamers that perturb the two-hybrid interaction.

In yet another embodiment of the invention, the starting strains in the input arrays can express a heterologous gene(s) from either a prokaryotic, viral, or eukaryotic genome. In a preferred embodiment, heterologous genes are from the human genome. Different alleles of these genes can be tested in yeast to see how they interact with mutated yeast genes that are homologous to human genes. This method can be used to assign function to different exogenous genes. Single nucleotide polymorphisms (SNPs) of human genes could also be characterized to identify SNP-dependent interactions. The genes of any organism could be similarly manipulated with this system. These heterologous genes can replace their deleted yeast homolog, or they can be genes that are not homologous to any yeast gene. These exogenous genes could be crossed with strains that contain either any of the genetic alterations described above, or any other genetic alteration.

Many yeast genes are conserved from yeast to humans and thus it is possible to functionally replace a yeast gene with its human homolog. There are many different alleles of a given human gene and some of these may be associated with a diseased state. The replacement of a yeast gene by set of alleles of its human homologue, each differing by one or more SNP (single nucleotide polymorphism), in the context of the described genetic arrays offers a means to assess the functional interactions of a given allele within a model eukaryotic cell. For example, the analysis of different alleles of a human gene may reveal that one allele in particular is associated with a greater number of synthetic lethal interactions, which suggests it is compromised for function relative to other alleles and, therefore, may be associated with a diseased state. If more than one conserved human gene is implicated in a diseased state, then in theory all combinations of different alleles can be tested for function within the context of a genetic array.

Yeast genetic arrays also permit the functional analysis of heterologous genes that do not have yeast counterparts. For example, consider a human gene, designated hXXX, whose product is involved in reorganization of the actin cytoskeleton and for which there is no yeast counterpart. Even though yeast cells do not contain a homolog hXXX, yeast cells have a highly conserved actin cytoskeleton and therefore will likely contain gene products, such as actin, that the hXXX gene product may interact with. Thus, expression of the human gene within the context of a yeast genetic array will likely result in synthetic lethal/fitness defects that link the function of hXXX to actin reorganization. The heterologous gene could be taken from any viral, prokaryotic, or other eukaryotic genome.

Starting strains carrying heterologous genes can be crossed with starting strains containing another exogenous gene, or any other genetic alteration. The genetic alterations in the other starting strain could be any of the ones defined above or any other genetic alterations. The phenotypes of these crosses can then be studied to determine if the resulting strains in the output array develop a synthetic fitness, or synthetic lethal phenotype, or any other discernible phenotype.

In another embodiment of the invention, the starting strains in the input array contain a promoter from either a prokaryotic, viral, or eukaryotic genome operably linked to a reference gene. Starting strains that carry a promoter operably linked to a reporter gene can be crossed with starting strains containing another promoter and reporter gene, or any other genetic alteration. The genetic alterations in the other starting strain can be any of the ones defined above or any other genetic alterations. The phenotypes of these crosses can then be studied to determine if the resulting strains in the output array develop a synthetic fitness, or synthetic lethal phenotype, synthetic dosage lethality, expression of the reporter gene, or lack thereof, or any other discernible phenotype.

The ability to control the expression levels of genes with regulated promoters is especially useful for synthetic dosage lethality screens. Synthetic dosage lethality is a specialized version of a classical synthetic lethality screen. In synthetic dosage lethality, a reference gene is overexpressed in set of mutant strains carrying potential target mutations. This reference gene can be an exogenous gene from a viral, prokaryotic, or eukaryotic genome. More specifically, the gene could be a human gene. Increasing the amount of the reference gene product may not produce a phenotype in a wild-type strain. However, a lethal phenotype may result when overexpression of a gene product is combined with decreased activity of another gene product that impinges on the same essential function. For example, synthetic dosage lethality has been used to identify genetic interactions between CTF3, which encodes a centromere binding protein, and a set of conditional kinetichore mutants. The synthetic dosage lethality gene could also contain single nucleotide polymorphisms.

Genes can be overexpressed by cloning the open reading frame (ORF) behind a strong promoter, such as the galactose-induced GAL1 promoter. Input arrays containing starting strains with the approximately 5,000 different yeast deletions can be crossed to a starting strain carrying a plasmid that contains a GAL1-regulated reference gene. Haploid meiotic progeny carrying GAL1-regulated reference gene and carrying the gene deletion can be selected. The output array containing yeast deletions combined with the GAL1-regulated reference gene can be pinned from glucose medium, where the reference gene is not expressed, to galactose medium, where it is overexpressed, to score for synthetic dosage lethality.

In another embodiment of the invention, the gene-encoding reporter, such as green fluorescence protein (GFP), may be placed on a plasmid under the control of a regulated promoter. One useful promoter is the pheromone-induced FUS1 promoter, FUS1pr, which is massively induced by stimulation of the MAP-kinase pathway that mediates the pheromone response in yeast. A FUS1pr-GFP gene could be constructed and introduced into the set of yeast deletion mutants for expression analysis. Mutations that lead to increased basal levels of FUS1pr-GFP expression, i.e. levels above that displayed by wild-type cells, would identify genes that encode potential negative regulators of the pheromone response signal transduction pathway. By contrast, mutations that lead to decreased basal levels of FUS1pr-GFP expression would identify genes that positively activate the activity of pheromone response pathway signaling molecules. Quantitative analysis of GFP expression can be achieved from agar-arrayed yeast colonies using a fluorimager as demonstrated by studies using the genome reporter matrix (GRM) constructed by Acacia Biosciences. In the GRM, plasmid-borne GFP was placed under the control of approximately 6,000 different yeast promoters and a high-density array of yeast colonies (wild-type cells) carrying the reporter constructs was monitored for genome-wide changes in gene expression in response to drug treatments.

In yet another embodiment of the invention, each of the yeast deletion mutants is constructed such that it is tagged with two unique 20 mer oligonucleotide sequences. These "bar codes" allow for identification and analysis of specific deletion mutants within large populations. A microarray printed with probes for the bar codes that correspond to the approximately 5,000 viable deletion mutants can be used to follow synthetic lethality of particular strains following batch mating and sporulation experiments. Microarray-based synthetic lethal analysis with bar-coded mutants follows the same series of steps outlined in the pinning procedure for double-mutant construction. However, in this case, the yeast mutants are manipulated as a pooled population of cells and the growth of the cells is monitored as an array of bar codes. Thus, if a bar code is included into the components of the genetic array, manipulations of the cells can be carried out in batch format for array analysis via the bar codes. Details of the bar-code methodology are described in Example 12.

The major advantage of the microarray approach to synthetic lethal analysis stems from its experimental simplicity. In the microarray approach, the approximately 5,000 viable deletion mutants are manipulated as a single pooled population, which eliminates the need for high-density arrays of mutants and the volumes of media associated with manipulations of these arrays. Thus, with access to bar-coded microarrays and the pooled mutants, individual labs should be able to carry out synthetic lethal screens rapidly. Overall, the parallel development of both the systematic and microarray-based approaches to synthetic lethal screening will allow for exploitation of the strengths of each strategy.

Described above are a variety of methods and composition for comprehensive double-mutant construction in yeast that relies upon genetic manipulation to introduce a marked mutation or plasmid into an ordered array of yeast mutants. In another embodiment, mutations and plasmids can be introduced into an input array via standard transformation procedures, e.g. lithium acetate or electroporation for the transformation of yeast cells. In this case, the resultant transformants would form the output array.

Defined genetic alterations can be combined using genetic manipulations or strain transformation protocols. In one embodiment of the invention, large-scale double-mutant combinations are constructed using a specialized starting strain and an automated pinning method for manipulation of high density input arrays of defined starting yeast mutants. The manipulations to be performed can be performed by a robot. Such robotic manipulations are described in detail in the examples, including Example 2. The development of robotic methods for manipulation of the budding yeast genome-wide deletion set will set the stage for exciting uses of the present invention. The high-density output arrays of multiple yeast strains of the present invention can be used in a variety of ways to analyze genetic interactions on a large-scale, high throughput basis. A description of some of these uses follows.

Synthetic Lethal Analysis of High Density Output Arrays Assigning Gene Function

Figure 3:
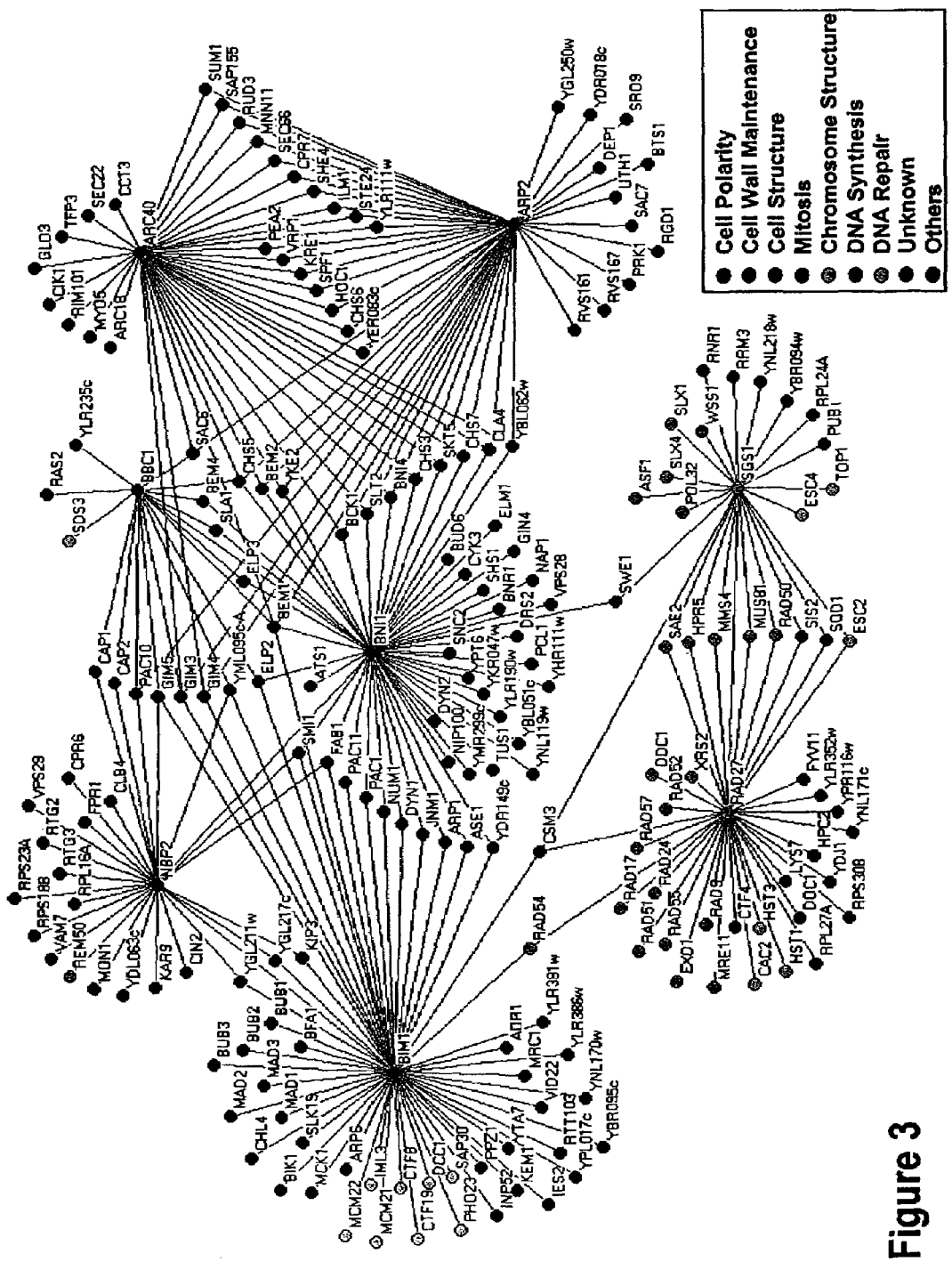
FIG. 3 illustrates a genetic network constructed from the interactions listed in Table 1. A genetic interaction network representing the synthetic lethal/sick interactions is determined by the synthetic genetic analysis of the present invention. Genes are represented as nodes and interactions are represented as edges that connect the nodes, 292 interactions and 205 genes are shown. The genes are colored according to their YPD cellular roles, with the most abundant cellular roles shown.
Figure 4:
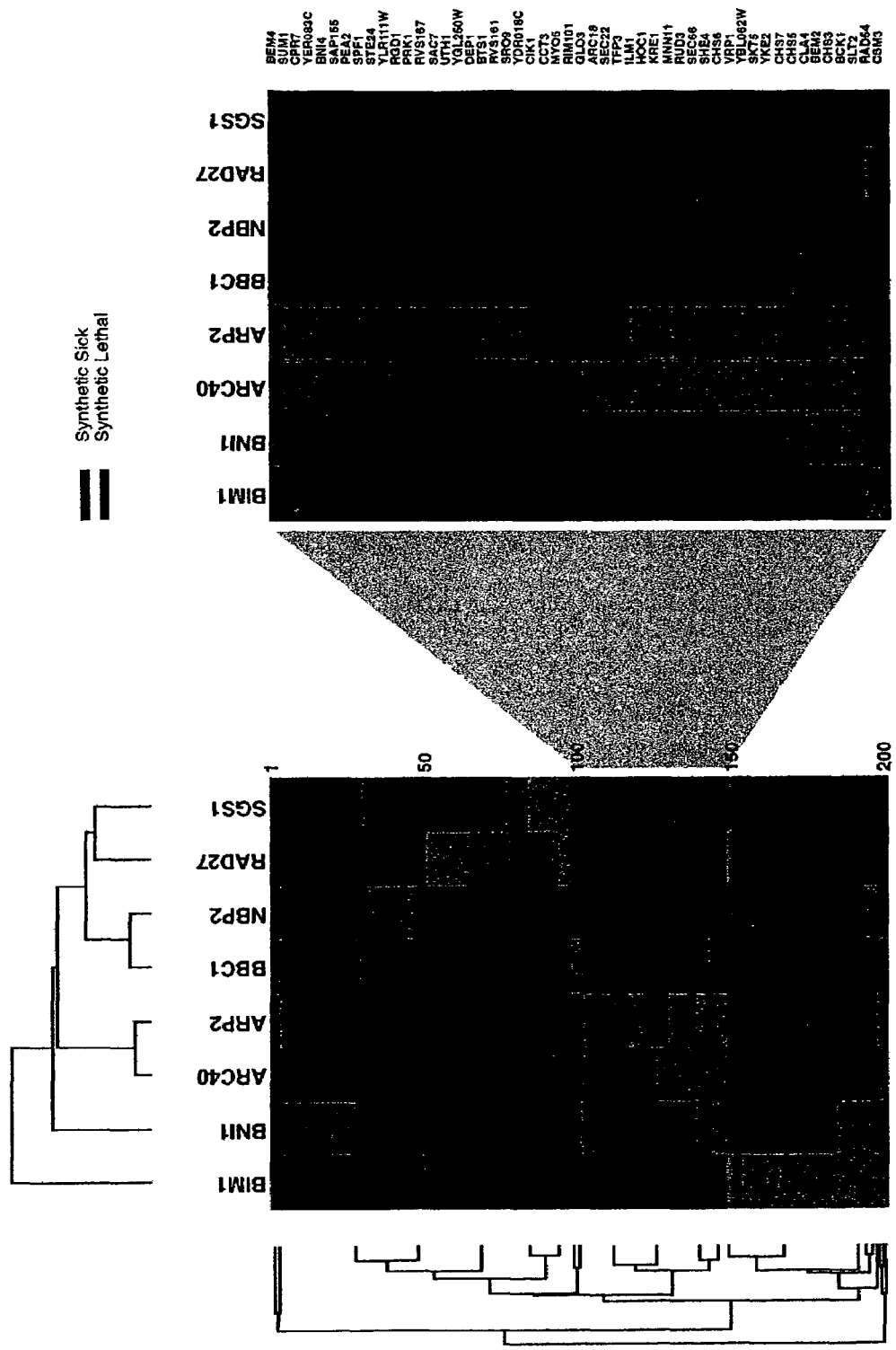
FIG. 4 illustrates two dimensional clustering analysis of synthetic lethal interactions. The set of synthetic lethal interactions associated with mutations in 8 query genes, BIM1, BNI1, ARC40, ARP2, NBP2, BBC1, RAD27 and SGS1, were plotted on the horizontal axis, with the query gene cluster tree above. The 201 genes that showed synthetic lethal interactions with the query genes were plotted on the vertical axis with the cluster tree on the leftmost side of the plot. Synthetic lethal and synthetic sick (slow growth) interactions are represented as shades. An expansion of the plot is shown to allow visualization of specific genes.

Mutations within many different yeast genes will lead to multiple synthetic lethal/fitness defects, generating a synthetic lethal profile for a given mutant. Cluster analysis of a set of synthetic lethal profiles should identify mutant alleles that result in similar compromised states and therefore perturb similar functions within the cell (FIG. 3 and FIG. 4). Thus, large-scale synthetic lethal/fitness analysis with yeast genetic arrays will provide a method of determining gene function. Mutations in nonessential genes are most easily analyzed; however, conditional alleles of essential genes, i.e. those genes required for cell growth, e.g. temperature sensitive alleles or those placed under the control of a regulated promoter (e.g. the Tet-regulated promoter), can be analyzed for synthetic effects following introduction into a genetic array. In the case of temperature sensitive alleles, the essential genes would be tested for synthetic lethal/fitness defects at a temperature below the nonpermissive/lethal temperature. For an essential gene under the control of a regulated promoter, synthetic lethal/fitness defects would be tested at an intermediate gene expression level, i.e. at a level that compromises fitness but does not prevent cell growth.

Synthetic Lethal Analysis of High Density Output Arrays for Drug Discovery And Potential Cancer Therapeutics The Seattle Project at the Fred Hutchison Cancer Research Center is founded on the concept that synthetic lethal analysis in model organisms provides a means to identify potential drug targets for cancer therapy. In this view, a null mutation represents a model for an ideal drug because in many cases it should mimic the effect of a highly specific inhibitor of the gene product. The identification of mutations that lead to a phenotype resembling a desired therapeutic outcome should thus also identify promising drug targets. Because the genes that control fundamental biological functions are often conserved, yeast and other model eukaryotes with sophisticated genetic methodology provide powerful systems for the identification of drug targets.

The rational identification of drugs for the treatment of particular forms of cancer or other diseases will likely stem from a knowledge of the mutations harbored by particular types of abnormal cells. In the context of anticancer drug therapeutics, the synthetic lethal analysis of a conserved yeast gene whose human homolog is often inactivated in tumors would identify potential targets for drug-induced inhibition. In this view, synthetic lethal analysis identifies genes whose inactivation results in cell death only within the context of another specific mutation and thus provides a potential program for killing cells within a diseased context.

Synthetic Lethal Analysis of High Density Output Arrays to Generate Cocktail Therapies If synthetic lethal/fitness analysis identifies novel gene deletion mutations that show a synthetic effect in combination with a known drug or mutant allele of a known drug target, then the identified genes may represent a new target for a drug that will enhance the effectiveness of the known drug. For example, if we identify gene deletion mutants that are hypersensitive to the growth inhibitory effects associated with Cisplatin, a cancer therapeutic agent, then inhibitors of the identified genes would represent potential targets for drugs that would be used in combination with Cisplatin to kill cancer cells. In another example, if we identify gene deletion mutants that were hypersensitive to an antifungal drug, then the inhibitors of the identified genes would represent potential targets for drugs that would used in combination with the antifungal drug to kill a fungal pathogen. This procedure could also be used with any genetic manipulation either defined above or elsewhere.

Synthetic Lethal Analysis of High Density Input Arrays Screened Against Small Molecules to Analyze Small Molecule-Target Interaction Comprehensive synthetic lethal analysis should provide us with a key for deciphering the interactions between small molecules and biological targets in yeast. In this scheme, the approximately 5,000 viable yeast disruption mutants are screened against small molecules of interest for synthetic drug sensitivity. If the sensitivity to a particular molecule resulted from the inactivation of a specific target then the synthetic drug sensitivity should mirror the synthetic lethal profile of the target gene. Thus, a comprehensive synthetic lethal profile provides a key for linking small molecules to biological targets in a whole cell growth assay.

The results of the comprehensive synthetic lethal analysis in yeast provide a whole cell screen for inhibitors of specific target molecules. For example, to search for inhibitors of a the PAK-like kinase Ste20p, we would simply screen for small molecules that specifically kill the panel of yeast mutants carrying deletion mutations that are synthetically lethal when combined with a ste20Δ mutation. The specificity of the screen will depend upon the specificity of the synthetic lethal profile associated with the ste20Δ mutation. Given that each mutation will be tested for synthetic lethality in approximately 5,000 different contexts, it is anticipated that even genes within the same pathway may show a distinct synthetic lethal profile.

Suppressor Analysis of a Conditional Lethal Situation

Genetic arrays can be used to identify mutations that function as suppressors of lethality. For example, consider a mutation in a gene whose product functions within a DNA damage check point signal transduction pathway. The combination of a DNA damage check point mutant and a DNA damaging agent leads to lethality and we can use a genetic array to screen for gene deletion mutations that suppress the conditional lethal situation. As another example, consider a gene that leads to lethality when overexpressed; in this case, we can use a genetic array to screen for mutations that are either hypersensitive or resistant to overexpression of the detrimental gene.

Genetic Mapping and Backcrossing the Yeast Deletion Mutations into Another Genetic Background Use of the synthetic genetic arrays of the present invention should also allow for backcrossing the entire set of deletion mutations into another genetic background to analyze traits specific to that background. Examples of genetic backgrounds which can be analyzed include the Σ1278 background that is competent for filamentous growth and the SK1 background that is hyperactive for sporulation.

Because haploid yeast double-mutants within the output array are formed by meiotic recombination, the analysis of strains within the output array can be used to map gain of function phenotypes, even those that are multigenic traits. In this case, the gene(s) associated with the gain of function phenotype would fail to form double mutants efficiently with genetically linked gene deletions, resulting in a series of output strains that fail to inherit the gain of function phenotype.

High Density Peptide Aptamer Mammalian Cell Microarrays

The synthetic genetic array analysis of the present invention can be extended from yeast cells to mammalian cells by using an array of transfection constructs that lead to the expression of peptide or nucleic acid aptamers or other genetic alterations. In the case of peptide aptamer expression, the peptide aptamer expression plasmids are first suspended in gelatin solution and arrayed on glass slides using a robotic microarrayer. Mammalian cells are then cultured on the glass slides containing the peptide aptamer expression plasmids. Cells growing in the vicinity of the gelatin spots uptake the peptide aptamer expression plasmids creating spots of localized transfection within a lawn of nontransfected cells. Once the peptide aptamer expression plasmids are incorporated into cells they can function as dominant agents, dominant agents being agents which perturb the function of the cell in any way.

In one example, an input starting mammalian cell line might carry a set of genes that allow for the formation and detection of a two-hybrid interaction and the input array might carry a set of peptide aptamer expression plasmids. In this case, the output array would consist of mammalian cells transfected with the aptamers that may perturb the two-hybrid interaction. The cell microarrays can be designed such that the positions of individual aptamers in the yeast array are cross-correlated to the positions of the same aptamers in the cell microarray. This correlation will allow aptamers that have observable phenotypes in the yeast array, much as the disruption of a mammalian protein interaction, to be directly assessed in the cell microarray.

As described above, there are numerous uses for the high density output arrays of multiple yeast strains of the present invention, including but not limited to synthetic lethal analysis of high density output arrays to assign gene function, synthetic lethal analysis of high density output arrays for drug discovery and potential cancer therapeutics, synthetic lethal analysis of high density output arrays to generate cocktail therapies, synthetic lethal analysis of high density input arrays screened against small molecules to analyze small molecule-target interaction, and suppressed analysis of a conditional lethal silation.

Synthetic Genetic Array Mapping (SGAM)

The synthetic genetic array analysis of the present invention can be used to map genes and mutations therein in yeast and other organisms. For example, any allele leading to an observable phenotype, such as an epistatic phenotype, e.g., one identifiable within a mixed population of cells resulting from the germination of both mutant and wild type spores, can be mapped using the SGA methodology. Such epistatic phenotypes include, but are not limited to: colony growth in an otherwise inviable genetic and/or environmental context, expression of chromophores, and morphogenetic phenotypes such as filamentous growth.

Figure 5:
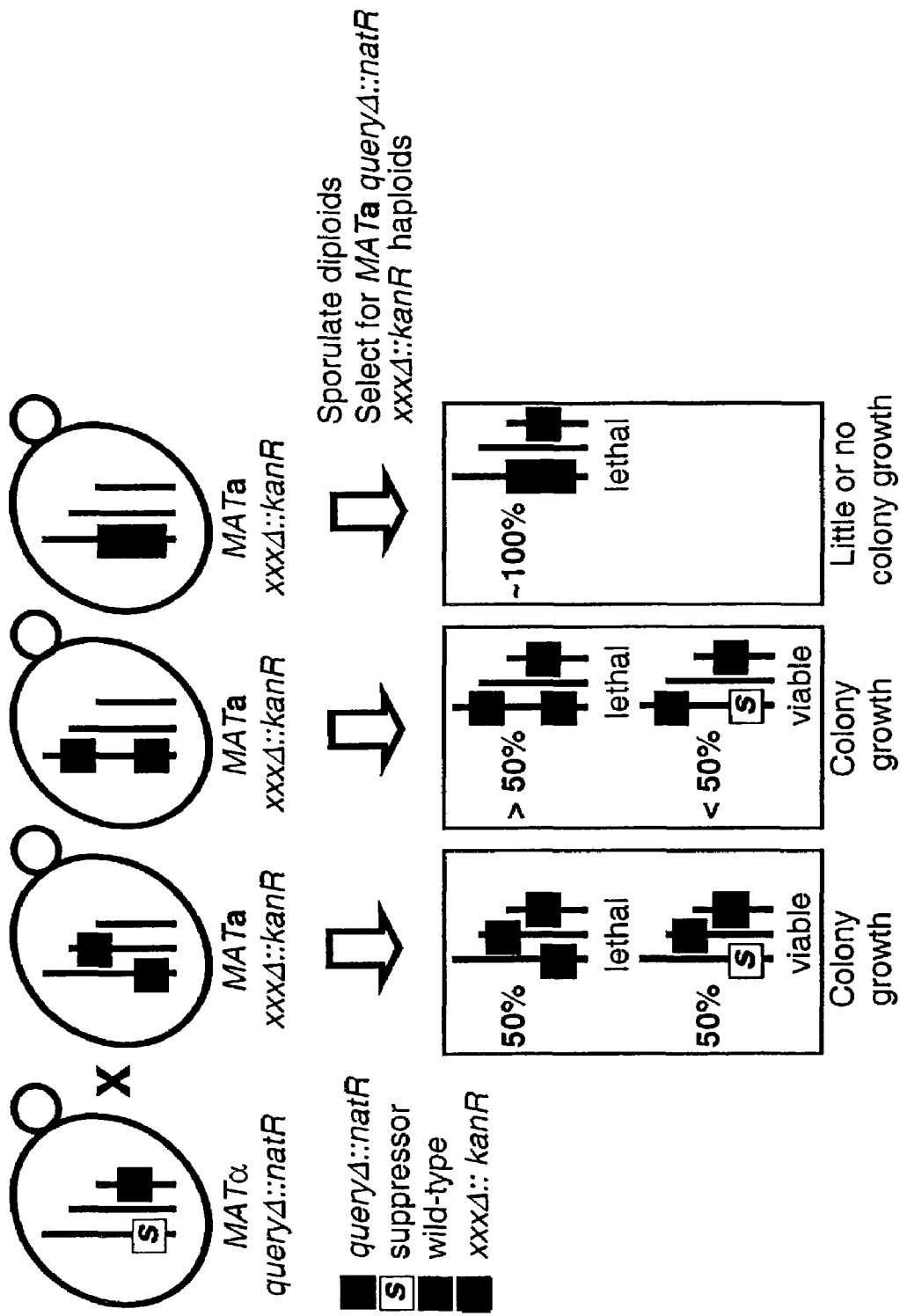
FIG. 5 is a schematic representation of behind SGA mapping (SGAM). As shown, SGA analysis is used to map the location of a mutant suppressor allele (s, open n box), which suppresses the lethality of a natR-marked gene deletion mutation (queryΔ::natR, k box). SGA analysis combines the natR-marked deletion mutation with ~5000 viable kanR-marked deletion mutations (xxxΔ::kanR, boxes, three right yeast) through mating, meiotic recombination, and germination of haploid MATa queryΔ::natR xxxΔ::kanR spore progeny. In deletion strains where the wild type allele (S, filled box) is tightly linked to the kanR-marked deletion (far right yeast), the low frequency of recombination between the suppressor allele (s) and the kanR-marked deletion will limit the recovery of viable $Nat^R$ $Kan^R$ double deletion progeny.

For example, FIG. 5 shows a schematic representation of an embodiment of the invention, where a haploid strain in which a suppressor mutation (s) in an unidentified gene (S) rescues the lethality associated with deletion of an essential gene (queryΔ::natR) marked with the dominant natR selectable marker. The viable double mutant starting strain (queryΔ::natR s) is crossed systematically to each of the ~5000 viable haploid deletion strains (xxxΔ::kanR) and the double deletion progeny (queryΔ::natR xxxΔ::kanR) selected. If, for a given kanR-marked deletion strain, the wild type allele (S) and the deletion (xxxΔ::kanR) are unlinked, 50% of the double deletion progeny (queryΔ::natR xxxΔ::kanR) will contain the suppressor mutation (s) and germinate to form a colony. In strains where the wild type allele (S) is tightly linked to the deleted gene (xxxΔ::kanR), the low frequency of recombination between the suppressor allele (s) and deleted gene (xxxΔ::kanR) will limit the recovery of viable double deletion progeny. The general chromosomal location of the suppressor allele (s) can thereby be identified by the failure to observe growth for a linked set of double deletion strains. In essence, to map the location of the mutation, SGAM employs a genome-wide and systematic set of two point crosses between the mutated allele and the marked deletion mutations (xxxΔ::kanR)

While other methods for mapping of mutations have been reported, SGAM is particularly useful, since although in certain embodiments the mutation is mapped by linkage to non-essential genes, it may lie in either non-essential or essential genes. To map mutations in essential genes, the allele must not cause lethality at the screening temperature and therefore can not be a null. Also, both dominant and recessive mutations can be mapped. Further, as the size of the linked group will be proportional to the frequency of meiosis in the parent diploid colonies, the assay can be adjusted by modulating sporulation efficiency. For instance, hampering the sporulation efficiency by manipulating temperature and/or incubation times should extend the linked region.

SGAM is also useful for the mapping of genes associated with multigenic traits, such as traits in which several alleles are required to confer the mutant phenotype, as linked groups lacking the mutant phenotype will form around each requisite allele. Additionally, SGAM allows the identification of the mutation within the mapped gene by sequencing of the gene(s) lying within the center of the linked group.

This invention will be further described in the following examples, which do not limit the scope of the invention described in the claims.

EXAMPLES

Example 1

Creation of Double Mutant Output Array

An example of a starting strain that could be used in this embodiment is the *Saccharomyces cerevesiae* strain termed Y2454. The Y2454 strain is characterized by being a MATα mating type with ura3, leu2, his3, and lys2 mutations, and a HIS3 gene linked to an MFA1 promoter. The ura3, leu2, his3, and lys2 mutations require the strain to be grown in supplemented media to survive. They also carry a can1 null allele which confers canavinine resistance to the cells. A mutant gene, for example, one of the approximately 5,000 non-lethal mutations found in *Saccharomyces cerevesiae*, is introduced into this strain. The deleted gene is being replaced by a NAT gene which confers noureseothricin resistance to these cells.

This strain can be crossed with a starting array of yeast strains of the MATa mating type. The strains in this starting array contain ura3, leu2, his3, and met15 knockouts, so that they can only survive on supplemented media. These cells can also contain a mutation of one of the approximately 5,000 non-lethal gene deletions known in *Saccharomyces cerevesiae*. The deleted gene is replaced with an operably linked KAN gene, which gives the yeast cells resistance to kanamycin derivatives like Geneticin. These starting array strains carry a wild-type CAN1 locus, which makes them sensitive to canavinine.

A double mutant haploid cell could then be developed by the following steps:

Step 1. Construction of a Y2454-derivative that carries a nat-marked mutant allele, e.g. bni1Δ::nat where the given gene is deleted and replaced with nat, which results in nourseothricin-resistance, for genome-wide synthetic lethal analysis.

Step 2. Mating of the MATα Y2454-derivative to the array of MATa xxxΔ::kan deletion mutants on rich medium to facilitate zygote formation.

Step 3. Transfer zygotes to medium containing geneticin and nourseothricin to select for growth of MATa/α diploid cells.

Step 4. Transfer MATa/α diploid cells to sporulation medium to induce spore formation.

Step 5. Transfer spores to synthetic medium lacking histidine and containing canavanine to select for growth MATa haploid spore-progeny.

Step 6. Transfer MATa haploid spore-progeny to medium containing geneticin and nourseothricin to score for growth and viability of MATa bni1Δ::nat xxxΔ::kan double-mutants.

In step 2, yeast cells are arrayed on rich medium to allow efficient mating. In step 3, the mating reactions are arrayed onto medium containing geneticin and nourseothricin, which allows for selected growth of diploid cells. In step 4, the diploid cells are transferred to medium that is low in nitrogen and carbon and induces sporulation. In step 5, the spores are transferred to germination medium that selects for growth of the haploid MATa cells (this step is described in detail below). In step 6, double mutant strains are selected for growth the two mutations are scored as synthetic lethal/fitness defect if the AMTa haploid double-mutants form a colony that is smaller than that associated with either of the single mutants. The mutations predicted to be synthetically lethal can be analyzed in more detail through tetrad analysis of the heterozygous diploid cells created in Step 2.

Example 2

Use of Robotics to Generate Output Array

Following construction of a natR-marked mutant for synthetic lethal analysis, simple replica plating or pinning manipulations will enable us to complete steps 2–6 of Example 1. These steps can be carried out through the use of a robotic colony arrayer, as described below. The Colony Arrayer used in this Example, the Virtek Vision CPCA was designed by our labs in conjunction with Virtek Vision. The CPCA is based upon a system used for genome-wide two-hybrid arrays, since the manipulations required for automated two-hybrid screens are very similar to those required for automated double-mutant construction and synthetic lethal screens.

For a rapid genome-wide two-hybrid screening procedure, we have created a robotic colony array which includes replica-plate pinhead that transfers 768 individual colonies from one standard microtiter-sized agar-slab plate to another in a single move. This cell density allows efficient mating, on the order of hundreds of zygotes formed per spot pinned, a frequency that will easily suffice for genome-wide synthetic lethal screens.

The general specifications of a colony arrayer are as follows:

1. 16 input and 16 output plates;

2. Replicating Pinning Head with 96, 384, or 768 pins, for high speed transfer of the colonies of different array density;

3. A gripper for handling the plates, and if desired for removing/replacing the covers for full automation;

4. Wash/Dry station for cleaning the pins between runs and includes the 5 stages of water, ethanol or bleach, sonicator (water), ethanol, and air-drying;

5. Controlled environment enclosure, with HEPA filter, humidifier, positive pressure and internal UV lamps to ensure full sterilization of the environment before arraying process.

Example 3

Recovery of Haploid Spore Progeny

The recovery of haploid spore progeny is mentioned in step 5 in Example 1, and is described in greater detail below. The MATα starting strain described in Example 1, Y2454, carries two selectable markers, can1Δ0 and MFA1pr-HIS3, both of which permit efficient recovery of haploid spore progeny.

i) MFA1pr-HIS3

MFA1 encodes the a-factor precursor, which is expressed constitutively in MATa cells. The MFA1 promoter, MFA1pr, is repressed in MATα and MATa/α cells. The MFA1pr-HIS3 reporter was constructed by replacing the MFA1 ORF (open reading frame) with the HIS3 ORF such that MFA1pr drives HIS3 expression. The MATα starting strain, Y2454, fails to grow on synthetic medium lacking histidine because the MFA1pr-HIS3 reporter is repressed in MATα cells. The cells constructed in step 2 of Example 1 will also fail to grow on synthetic medium lacking histidine because the MFA1pr-HIS3 reporter is repressed in MAT a/α cells. Following sporulation of the diploid cells in Step 4 of Example 1, the MFA1pr-HIS3 reporter selects for growth of MATa haploid progeny. Twenty-five per cent of the haploid progeny generated by sporulation of the diploid cells will be AMTa MFA1pr-HIS3. Other a-specific reporters can be constructed using promoters from different a-specific genes (e.g. MFA2, ASG7, STE2) or different reporters (e.g. URA3, LEU2, or heterologous genes conferring resistance to antibiotics or other chemicals)

ii) can1Δ0

The CAN1 gene encodes an arginine permease. The Y2454 starting strain has been engineered to carry a recessive can1Δ0 null allele, which renders the cells resistant to canavanine, a toxic arginine analog that is transported by the CAN1 gene product. The knock-out strains constructed by the deletion consortium are canavanine-sensitive because they carry a wild-type CAN1 locus. The MATα starting strain, Y2454, carries can1Δ0 rendering it canavanine-resistant. The MATa/α can1Δ0/CAN1 diploids isolated in step 3 of Example 1 will be canavanine-sensitive. Following sporulation of the diploid cells in step 4 of Example 1, the can1Δ0 allele allows for selection of canavanine-resistant haploid progeny. Fifty percent the haploid spore progeny will be canavanine-resistant. Other recessive drug resistant genes, such as cyh2 mutations which leads to cycloheximide resistance, can also be used.

Efficient Selection for Haploid Spore Progeny

Both the can1Δ0 and the MFA1pr-HIS3 reporter allow selection for haploid spore progeny in Step 5 of the pinning procedure described in Example 1. The selection provided by the MFA1pr-HIS3 reporter enables the specific isolation of MATa cells. It is important to isolate spore progeny of a single mating type when ultimately scoring for the presence or absence of two marked mutant alleles; otherwise progeny of opposite mating type may conjugate to generate diploid cells heterozygous for each mutation, which would appear, perhaps falsely, as a viable double-mutant.

Initially, we tested if the MFA1pr-HIS3 reporter would suffice for isolation of MATa haploid spore progeny in step 5. These tests revealed that, prior to incubation on sporulation medium, a fraction of the AATa/α MFA1-HIS3/MFA1 cells became competent for growth on medium lacking histidine. This process appears to involve mitotic recombination between the centromere and the MAT locus on chromosome III, creating MATa/a MFA1-HIS3 cells, which express MFA1-HIS3 and grow on medium lacking histidine. In a synthetic lethal screen, these MATa/a diploid cells would be heterozygous for the NAT-marked and the KAN-marked alleles and appear as viable double-mutant haploid cells. To overcome this problem, we introduced a can1Δ0 mutation into our starting strain; can1 mutant alleles have been used extensively to select for canavanine-resistant haploids in random spore analysis. Analogously, the MATa/α can1Δ0/CAN1 MFA1pr-HIS3/MFA1 diploids, constructed in steps 2 and 3, can become canavanine-resistant as diploid cells through mitotic recombination involving the can1Δ0 locus, creating AMTa/α can1Δ0/can1Δ0 MFA1pr-HIS3/MFA1 cells. Importantly, prior to incubation on sporulation medium, we do not observe the formation of cells that are both canavanine-resistant and competent for growth on medium lacking histidine. Thus, the frequency of these two distinct mitotic recombination events is below the level of detection and we will not observe MATa/a can1Δ0/can1Δ0 MFA1pr-HIS3/MFA1 cells as background during a synthetic lethal screen.

Example 4

Genetic Exceptions 4A. xxxΔ::kanR Deletion Mutations Linked to MFA1pr-HIS3 or can1Δ

While the MFA1pr-HIS3 and the can1Δ alleles are essential for synthetic lethal analysis via a pinning procedure, they present a position-based problem. The xxxΔ::KANR deletion mutations that are linked tightly to these alleles will be paired into the genome of the haploid spores at reduced frequency and may lead to a false synthetic lethal score. However, because the position of every ORF is defined precisely, the problematic double-mutant combinations are predictable. For mutations in the vicinity of MFA1pr-HIS3 on chromosome X, we will employ an MFA2pr-HIS3 starting strain. The MFA2 gene encodes a second copy of the a-factor structural gene. Like MFA1pr, MFA2pr leads to a-specific gene expression and will facilitate selection for MATa spores. Because 1 cM in *S. cerevisiae* is roughly equivalent to 1.5 Kb of DNA sequence and the average *S. cerevisiae* gene is approximately 2 Kb, we anticipate that 10–30 genes on either side of the MFA1 locus will have to be mated to a starting strain containing MFA2pr-HIS3. Alternatively the MFA1pr-HIS3 could be moved to another position in the genome. The can1Δ0 allele presents a slightly different problem because it cannot be moved like the MATa-specific reporter. To solve this problem, we will directly introduce the can1Δ allele into approximately 10–30 of the xxxΔ::kanR deletion mutants on either side of the CAN1 locus. Alternatively, we could employ another recessive drug resistant marker, e.g. cyh2.

4B. Genetic Interactions with Selection Genes

Some xxxΔ::kanR deletion mutations may cause synthetic lethality in synthetic lethal starting strains carrying the MFA1pr-HIS3 and can1Δ alleles. Because MFA1 is a specialized gene devoted to conjugation, it is unlikely that MFA1pr-HIS3 will be associated with any synthetic lethal interactions unless localized alterations of the genome affect the function of neighboring genes. Because the CAN1 gene product facilitates arginine uptake, the can1Δ deletion mutation will be synthetically lethal with any gene that prevents arginine biosynthesis. All the genes required for arginine biosynthesis will be defined/confirmed simply by creating all the double mutants with the wild-type version of the starting strain.

4C. Defects in Mating and Spore Formation

Some xxxΔ::KANR deletion mutations will be defective for one of the cellular functions required for double mutant construction or spore formation. For example, mating defective mutants (e.g. ste4Δ) will fail to form diploids in Step 2 of the pinning procedure. A genome-wide synthetic lethal screen will also identify all the genes required for sporulation in Step 4. Obviously, diploids that are homozygous for certain mutations will lead to a sporulation defect; however, other genes may prove haploinsufficient for sporulation or two mutations may exhibit nonallelic-noncomplementation, giving rise to a sporulation defect. To distinguish the mutants defective for these functions, analysis of the growth of MATa MFA1pr-HIS3 can1Δ0 cells in Step 5 will be important.

Example 5

Comprehensive Synthetic Lethal Screen in Yeast

A large-scale comprehensive synthetic lethal analysis can be performed either by constructing approximately 5,000 gene deletions in the synthetic lethal starting strain, Y2454, or by establishing an automated method to transfer the knockout alleles constructed by the deletion consortium into the Y2454 starting strain. In this example, we utilize an automated introduction of the deletion consortium knockout alleles into a synthetic lethal starting strain. First we switch each kanR-marked allele to a natR-marked allele and then select for the presence of MFA1pr-HIS3 in the MATα synthetic lethal starting strain following a genetic cross and a series of pinning steps.

Switching the kanR-marked allele to a natR-marked allele is achieved easily through transformation of xxxΔ::KAN strains with a kanR-natR switcher-cassette, in which the natR gene has been engineered so that it is flanked by sequences within the original kanR disruption cassette, and subsequent screening of the nat-resistance transformants for kanamycin sensitivity. Strain growth and transformation will be carried out using a 96 well format; therefore, approximately 52 rounds of transformation will allow us to switch the panel of approximately 5000 viable AMTa ura3Δ0 leu2Δ0 his3Δ1 met15Δ0 xxxΔ::kan strains to MATa ura3Δ0 leu 2Δ0 his3Δ1 met15Δ0 xxxΔ::nat strains.

The next challenge is to move the approximately 5,000 xxxΔ::nat alleles from the MATa ura3Δ0 leu2Δ0 his3Δ1 met15Δ0 xxxΔ::nat cells into the strain that carries the haploid select alleles, MFA1pr-HIS3 and can1Δ0. Of the alleles specific for the MATα strain, lys2Δ0 and can1Δ0 are associated with drug-mediated selections; however, we must construct a haploid selection marker that is functionally equivalent to MFA1pr-HIS3 and selects specifically for growth of MATα cells.

Construction of two tightly linked reporters, one that selects for MATa cells and another that selects for MATα cells, provides a solution to this problem. A dual reporter, MFA1pr-HIS3::MFα1pr-LEU2, will be created simply by integrating MFα1pr-LEU2 just downstream of MFA1pr-HIS3. As described above, the MFA1pr-HIS3 reporter provides a selection for haploid MATa cells on medium lacking histidine. MFα1pr controls the expression of the α-factor structural gene and is expressed only in MATα cells. MFα1pr-LEU2 provides a selection for MATα cells on synthetic medium lacking leucine. Because MFA1pr-HIS3 is tightly linked to MFα1pr-LEU2 within the context of the dual reporter, the MATα cells recovered on synthetic medium lacking leucine will also carry MFA1pr-HIS3. Several variations of this theme are possible. For example, the MFA1pr-HIS3 could be placed at CAN1 locus, creating can1Δ0::MFA1pr-HIS3; in this context, growth of MATα MFα1pr-LEU2 can1Δ0::MFA1pr-HIS3 cells can be selected on synthetic medium containing canavanine and lacking leucine.

Experimental Steps for a 5,000×5,000 Genome-wide Synthetic Lethal Screen

Step 1. 96-well format transformation will be used to switch a panel of approximately 5000 viable MATa ura3Δ0 leu2Δ0 his3Δ1 met15Δ xxxΔ::kanR strains to MATa ura3Δ0 leu2Δ0 his3Δ1 met15Δ0 xxxΔ::NAT strains. Transformants that grow on medium containing nourseothricin will be screened for Geneticin sensitivity to confirm the switching event.

Step 2. The MATa ura3Δ0 leu2Δ0 his3Δ1 met15Δ0 xxxΔ::natR strains will be mated to MATα ura3Δ0 leu2Δ0 his3Δ1 lys2Δ0 MFA1pr-HIS3::MFα1pr-URA3 can1Δ0 on rich medium. The resultant diploid cells will be selected for growth on synthetic medium lacking methionine and lysine. As mentioned above, this selection is not ideal because the met15Δ0 allele does not completely eliminate growth on medium lacking methionine; however, because each strain will only require mating once, we will be able to follow the diploid selection carefully using relatively large patches of cells and double replica plating to selective medium.

Step 3. Sporulation of the resultant diploid cells and selection for MATα ura3Δ0 leu2Δ0 his3Δ1 lys2Δ0 MFA1pr-HIS3::MFα1pr-URA3 can1Δ xxxΔ::LEU2 on medium that lacks uracil and leucine but contains α-aminoadipate and canavanine. α-aminoadipate selects for lys2Δ0 mutant cells and canavanine selects for can1Δ0 cells; 50% of the resultant haploids will be met15Δ0. The presence of the met15 marker can be scored by successive replica-platings to medium lacking methionine.

Step 4. Each of the approximately 5000 MATα ura3Δ0 leu2Δ0 his3Δ1 lys2Δ0 MFA1pr-HIS3::MFα1pr-URA3 can1Δ xxxΔ::LEU2 strains will each be mated to the array of MATa xxxΔ::KANR deletion mutants and run through steps 2–6 of the pinning procedure outlined in Example 1 for systematic genome-wide synthetic lethal analysis.

Example 6

Input Array of 5,000 Strains Crossed with Particular Mutation

In a large-scale application of the synthetic genetic analysis of the present invention, we screened a bni1Δ query mutation against an array of 4,644 different viable deletion strains. The array was propagated on a set of agar plates at a density of 384 strains per plate. For screening, the array was first pinned manually and subsequently adapted for high-throughput automation using robotics that we designed specifically for the manipulation of high density yeast arrays. To ensure reproducibility within a screen and to facilitate visual scoring, each gene deletion strain was arrayed in pairs, at 768 strains per plate. We scored 67 potential synthetic lethal/sick interactions, 51 (76%) of which were confirmed by tetrad analysis. To group the identified genes by functional classification, we assembled a list of their cellular roles defined by the Yeast Proteome Database. As shown in Table 1, these interactions were highly enriched for genes with roles in cell polarity (20%) cell wall maintenance (18%), and mitosis (16%). Pathways critical for the fitness of bni1Δ cells were revealed by multiple interactions with subsets of genes involved in bud emergence (BEM1, BEM2, and BEM4), chitin synthase III activity (CHS3, SKT5, CHS5, CHS7, and BNI4), MAP kinase pathway signaling (BCK1 and SLT2), the cell cycle-dependent transition from apical to isotropic bud growth (CLA4, ELM1, GIN4, and NAP1), and the dynein/dynactin spindle orientation pathway (DYN1, DYN2, PAC1, PAC11, ARP1, JNM1, NIP100). Importantly, we identified 8 of the 10 previously known bni1Δ synthetic lethal/sick interactions, which include BNR1, HOF1, CDC12, SLT2, BCK1, PKC1, genes implicated in polarized morphogenesis and cell wall maintenance, and ASE1, DYN1, ARP1, NIP100, genes implicated in mitotic spindle function. Of those that were not identified, CDC12 and PKC1 were not contained in our deletion set, while cells lacking HOF1 grow very slowly and are apparently beyond the sensitivity of the assay. In total, we discovered 42 novel synthetic genetic interactions for bni1 Δ, including 10 genes of unclassified function.

Table 1 below lists a set of synthetic lethal/sick interactions observed for query mutations in BNI1, ARC40, BBC1, NBP2, BIM1, RAD27, and SGS1.

TABLE 1

| | Cell Role |
|---|---|
| BNI1 | |
| BEM1 | Cell Polarity |
| BEM2 | Cell Polarity |
| BEM4 | Cell Polarity |
| BUD6† | Cell Polarity |
| SLA1† | Cell Polarity |
| CLA4 | Cell Polarity |
| ELM1† | Cell Polarity |
| GIN4 | Cell Polarity |
| NAP1† | Cell Polarity |
| SWE1† | Cell Polarity |
| BNR1 | Cytokinesis |
| CYK3† | Cytokinesis |
| SHS1 | Cytokinesis |
| BCK1 | Cell Wall Maintenance |
| BNI4† | Cell Wall Maintenance |
| FAB1 | Cell Wall Maintenance |
| CHS3 | Cell Wall Maintenance |
| SKT5† | Cell Wall Maintenance |
| CHS5† | Cell Wall Maintenance |
| CHS7† | Cell Wall Maintenance |
| SLT2 | Cell Wall Maintenance |
| SMI1† | Cell Wall Maintenance |
| ARP1 | Mitosis |
| ASE1 | Mitosis |
| DYN1 | Mitosis |
| DYN2† | Mitosis |
| JNM1 | Mitosis |
| NIP100 | Mitosis |
| NUM1 | Mitosis |
| PAC1 | Mitosis |
| ATS1 | Cell Structure |
| PAC11 | Cell Structure |
| YKE2† | Cell Structure |
| PCL1† | Cell Cycle Control |
| DRS2 | RNA Processing |
| SNC2 | Vesicular Transport |
| VPS28 | Vesicular Transport |
| YPT6† | Vesicular Transport |

TABLE 1-continued

| | Cell Role |
|---|---|
| ELP2 | Pol II Transcription |
| ELP3† | Pol II Transcription |
| BBC1† | Unknown |
| NBP2† | Unknown |
| TUS1† | Unknown |
| YBL051c† | Unknown |
| YBL062w† | Unknown |
| YDR149c | Unknown |
| YHR111w† | Unknown |
| YKR047w† | Unknown |
| YLR190w† | Unknown |
| YMR299c† | Unknown |
| YNL119w† | Unknown |
| BBC1 | |
| BEM1 | Cell Polarity |
| BEM4 | Cell Polarity |
| BNI1† | Cell Polarity |
| SLA1† | Cell Polarity |
| CAP1† | Cell Structure |
| CAP2† | Cell Structure |
| PAC10† | Cell Structure |
| GIM3 | Cell Structure |
| GIM5 | Cell Structure |
| SAC6 | Cell Structure |
| CHS5† | Cell Wall Maintenance |
| RAS2 | Signal Transduction |
| ELP2† | Pol II Transcription |
| ELP3† | Pol II Transcription |
| SDS3 | Chromatin Structure |
| YLR235c | Unknown |
| YML095c-A | Unknown |
| ARC40 | |
| ARC18 | Cell Polarity |
| BEM1 | Cell Polarity |
| BEM2 | Cell Polarity |
| CLA4 | Cell Polarity |
| MYO5† | Cell Polarity |
| PEA2† | Cell Polarity |
| VRP1 | Cell Polarity |
| BCK1 | Cell Wall Maintenance |
| BNI4† | Cell Wall Maintenance |
| CHS3 | Cell Wall Maintenance |
| SKT5 | Cell Wall Maintenance |
| CHS5 | Cell Wall Maintenance |
| CHS6 | Cell Wall Maintenance |
| CHS7 | Cell Wall Maintenance |
| HOC1 | Cell Wall Maintenance |
| KRE1 | Cell Wall Maintenance |
| SLT2 | Cell Wall Maintenance |
| SPF1† | Cell Wall Maintenance |
| YER083c† | Cell Wall Maintenance |
| YKE2 | Cell Structure |
| GIM3 | Cell Structure |
| GIM4† | Cell Structure |
| CCT3† | Cell Structure |
| SAC6 | Cell Structure |
| GLO3 | Vesicular Transport |
| SAP155† | Cell Cycle Control |
| SEC66 | Protein Modification |
| ILM1 | Energy Generation |
| MNN11 | Protein Modification |
| STE24† | Protein Modification |
| CIK1† | Meiosis |
| RIM101† | Meiosis |
| RUD3 | Vesicular Transport |
| SEC22 | Vesicular Transport |
| TFP3 | Small Molecule Transport |
| CPR7† | Protein Folding |
| SHE4 | Differentiation |
| SUM1† | Pol II Transcription |
| YBL062w | Unknown |
| YLR111w† | Unknown |
| ARP2 | |
| BEM1† | Cell Polarity |

TABLE 1-continued

| | Cell Role |
|---|---|
| BEM2† | Cell Polarity |
| CLA4† | Cell Polarity |
| PEA2† | Cell Polarity |
| PRK1† | Cell Polarity |
| RGD1† | Cell Polarity |
| RVS161 | Cell Polarity |
| RVS167† | Cell Polarity |
| VRP1† | Cell Polarity |
| BCK1 | Cell Wall Maintenance |
| BNI4 | Cell Wall Maintenance |
| CHS3 | Cell Wall Maintenance |
| SKT5 | Cell Wall Maintenance |
| CHS5† | Cell Wall Maintenance |
| CHS6† | Cell Wall Maintenance |
| CHS7† | Cell Wall Maintenance |
| HOC1 | Cell Wall Maintenance |
| KRE1 | Cell Wall Maintenance |
| SLT2 | Cell Wall Maintenance |
| SPF1† | Cell Wall Maintenance |
| YER083c | Cell Wall Maintenance |
| YKE2 | Cell Structure |
| PAC10 | Cell Structure |
| GIM3 | Cell Structure |
| GIM4 | Cell Structure |
| SAC6 | Cell Structure |
| SAC7† | Cell Structure |
| ILM1 | Energy Generation |
| SAP155† | Cell Cycle Control |
| SEC66 | Protein Modification |
| MNN11 | Protein Modification |
| STE24† | Protein Modification |
| BTS1 | Protein Modification |
| RUD3 | Vesicular Transport |
| CPR7 | Protein Folding |
| SHE4† | Differentiation |
| SUM1 | Pol II Transcription |
| SRO9 | Protein Synthesis |
| UTH1† | Aging |
| DEP1 | Lipid Metabolism |
| YBL062w | Unknown |
| YDR018c | Unknown |
| YGL250w† | Unknown |
| YLR111w† | Unknown |
| BIM1 | |
| ARP1 | Mitosis |
| ASE1 | Mitosis |
| BIK1 | Mitosis |
| CHL4 | Mitosis |
| DYN1 | Mitosis |
| JNM1 | Mitosis |
| KIP3 | Mitosis |
| NUM1 | Mitosis |
| PAC1 | Mitosis |
| SLK19 | Mitosis |
| BFA1 | Mitosis |
| BUB1 | Mitosis |
| BUB2 | Mitosis |
| BUB3 | Mitosis |
| MAD1 | Mitosis |
| MAD2 | Mitosis |
| MAD3 | Mitosis |
| CSM3 | Meiosis |
| MCK1 | Meiosis |
| CTF8 | Chromatin Structure |
| CTF19 | Chromatin Structure |
| DCC1 | Chromatin Structure |
| IML3 | Chromatin Structure |
| MCM21 | Chromatin Structure |
| MCM22 | Chromatin Structure |
| PHO23 | Chromatin Structure |
| SAP30 | Chromatin Structure |
| BEM1 | Cell Polarity |
| ARP6† | Cell Structure |
| GIM3 | Cell Structure |
| GIM4 | Cell Structure |
| GIM5 | Cell Structure |
| PAC11 | Cell Structure |
| FAB1 | Cell Wall Maintenance |
| SMI1 | Cell Wall Maintenance |
| ELP2 | Pol II Transcription |
| INP52 | Vesicular Transport |
| RAD54 | DNA Repair |
| PPZ1 | Signal Transduction |
| KEM1 | RNA Processing |
| AOR1 | Unknown |
| IES2† | Unknown |
| MRC1 | Unknown |
| RTT103† | Unknown |
| VID22 | Unknown |
| YTA7 | Unknown |
| YBR095c | Unknown |
| YDR149c | Unknown |
| YGL211w† | Unknown |
| YGL217c | Unknown |
| YNL170w | Unknown |
| YLR381w | Unknown |
| YLR386w | Unknown |
| YML095c-A | Unknown |
| YPL017c | Unknown |
| NBP2 | |
| BIM1 | Mitosis |
| CIN2† | Mitosis |
| KAR9 | Mitosis |
| KIP3 | Mitosis |
| PAC10 | Cell Structure |
| GIM5 | Cell Structure |
| CAP1† | Cell Structure |
| CAP2† | Cell Structure |
| BNI1† | Cell Polarity |
| FAB1 | Cell Wall Maintenance |
| SMI1† | Cell Wall Maintenance |
| VAM7† | Vesicular Transport |
| VPS29† | Vesicular Transport |
| RPL16A† | Protein Synthesis |
| RPS18B† | Protein Synthesis |
| RPS23A† | Protein Synthesis |
| CPR6† | Protein Folding |
| FPR1† | Protein Folding |
| CLB4† | Cell Cycle Control |
| REM50† | DNA Repair |
| RTG2† | Carbohydrate Metabolism |
| RTG3† | Carbohydrate Metabolism |
| MON1† | Unknown |
| YDL063c† | Unknown |
| YGL211w† | Unknown |
| YGL217c | Unknown |
| YML095c-A | Unknown |
| SGS1 | |
| ASF1† | DNA Repair |
| HPR5 | DNA Repair |
| POL32 | DNA Repair |
| RAD27 | DNA Repair |
| RAD50 | DNA Repair |
| SAE2 | DNA Repair |
| SLX1 | DNA Repair |
| MMS4 | DNA Repair |
| MUS81 | DNA Repair |
| SLX4 | DNA Repair |
| WSS1 | DNA Repair |
| RNR1 | DNA Synthesis |
| RRM3 | DNA Synthesis |
| YNL218w† | DNA Synthesis |
| CSM3† | Meiosis |
| ESC2† | Chromatin Structure |
| ESC4† | Chromatin Structure |
| TOP1† | Chromatin Structure |
| SWE1† | Cell Cycle Control |
| PUB1† | RNA Processing |
| RPL24A† | Protein Synthesis |
| SIS2† | Cell Stress |
| SOD1 | Cell Stress |

TABLE 1-continued

| | Cell Role |
|---|---|
| YBR094w | Unknown |
| RAD27 | |
| DDC1[†] | DNA Repair |
| EXO1[†] | DNA Repair |
| HPR5 | DNA Repair |
| MRE11 | DNA Repair |
| MMS4[†] | DNA Repair |
| MUS81[†] | DNA Repair |
| RAD9 | DNA Repair |
| RAD17[†] | DNA Repair |
| RAD24[†] | DNA Repair |
| RAD50 | DNA Repair |
| RAD51 | DNA Repair |
| RAD52 | DNA Repair |
| RAD54 | DNA Repair |
| RAD55 | DNA Repair |
| RAD57 | DNA Repair |
| SAE2 | DNA Repair |
| XRS2 | DNA Repair |
| CTF4[†] | DNA Synthesis |
| CAC2[†] | Chromatin Structure |
| ESC2[†] | Chromatin Structure |
| HST1[†] | Chromatin Structure |
| HST3[†] | Chromatin Structure |
| HPC2[†] | Pol II Transcription |
| CSM3[†] | Meiosis |
| DOC1 | Cell Cycle Control |
| RPL27A | Protein Synthesis |
| RPS30B[†] | Protein Synthesis |
| YDJ1 | Protein Translocation |
| LYS7 | Cell Stress |
| SIS2[†] | Cell Stress |
| SOD1 | Cell Stress |
| FYV11 | Unknown |
| YLR352w[†] | Unknown |
| YNL171c | Unknown |
| YPR116w | Unknown |

Example 7

Demonstration that Pinning Procedure Works for Synthetic Lethal Analysis

The present example demonstrates that the replica pinning procedure of the present invention can be used for synthetic lethal analysis. A deletion of the BNI1 gene, bni1Δ, was selected as the query mutation. A test-array of gene deletion mutants was assembled that included bnr1Δ, which is synthetically lethal with bni1Δ. BNI1 and BNR1 both encode members of the formin family, proteins that appear to control actin polymerization in response to signaling by Rho-type GTPases. Growing yeast cells contain two major filamentous actin structures, cortical actin patches, which polarize to the cortex of the growing bud and act as sites of endocytosis, and actin cables, which align along the mother bud axis and act as tracks for myosin motors that coordinate polarized cell growth and spindle orientation. Bni1 and Bnr1 are required for the formation of actin cables. bni1Δ mutants show defects in polarized cell growth and spindle orientation, whereas bnr1Δ mutants display no obvious phenotype, indicating that Bni1 functions as the predominant formin in yeast cells. The array contained 96 strains, each of which was included in quadruplicate and positioned next to each other in a square pattern, resulting in a matrix with 384 elements. bnr1Δ was included at two positions and enriched the array for mutations in other genes with roles in actin assembly and cell polarity.

Figure 2:
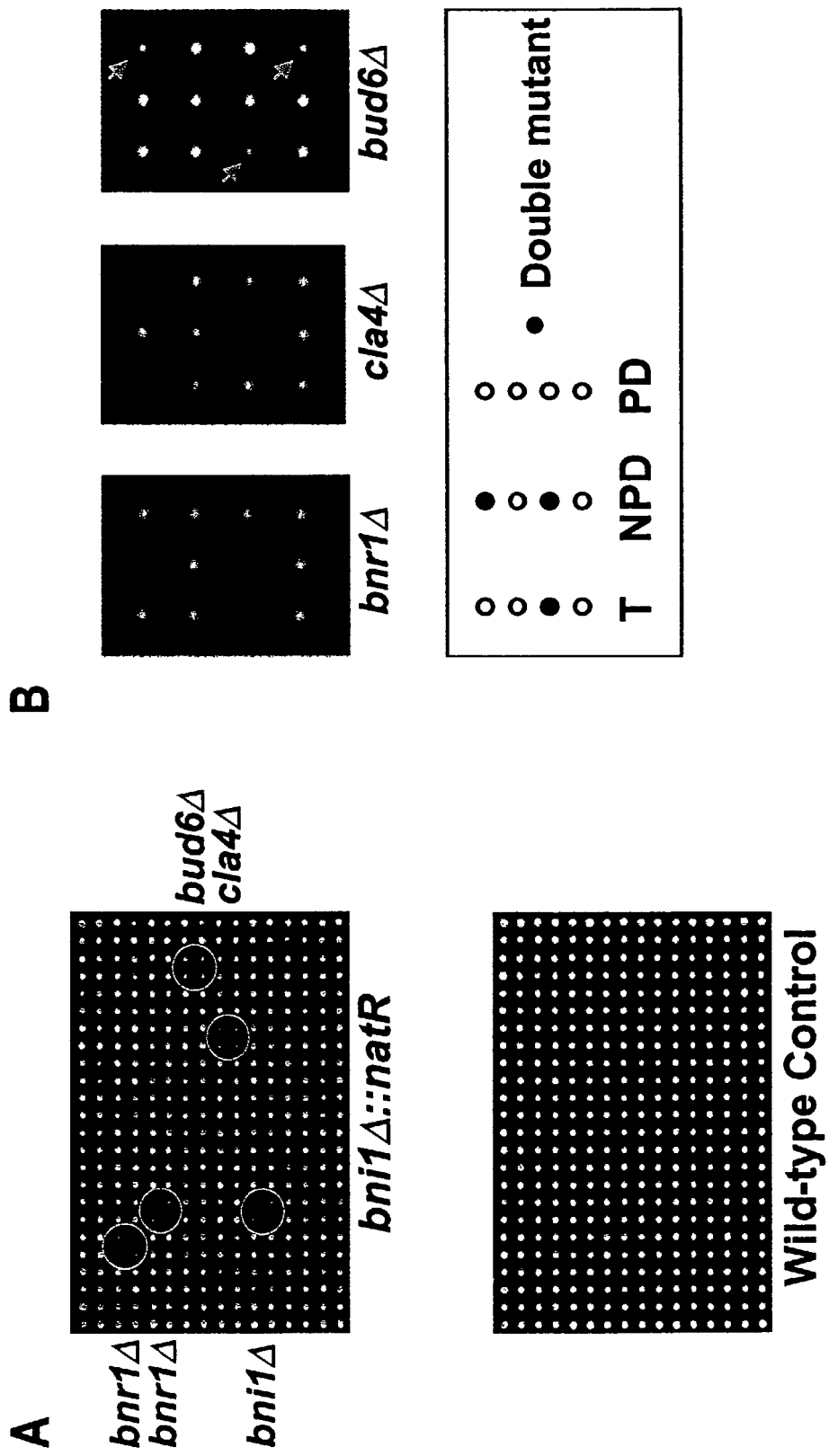
FIG. 2A illustrates the array of bni1Δ double mutants resulting from the final pinning and the corresponding wild-type control.
FIG. 2B illustrates that both the bni1Δ bnr1 Δ and bni1Δ cla4Δ double-mutants were inviable and that the bni1Δ bud6Δ double-mutant was associated with a slower growth rate or "synthetic sick" phenotype, reflecting reduced fitness of the double-mutant relative to the respective single mutants.

The array of bni1Δ double-mutants resulting from the final pinning and the corresponding wild-type control are shown in FIG. 2A. As anticipated, the cells at the bnr1Δ positions failed to grow, forming a residual colony with a reduced size relative to the control. Because the resultant double-mutants are created by meiotic recombination, gene deletions that are genetically linked to the query mutation form double mutants at a reduced frequency. Moreover, when the query mutation is actually identical to one of the gene deletions within the array, double mutants can not form. Thus, we also anticipated that the cells at the bni1Δ position would fail to grow under double-mutant selection. Novel synthetic genetic interactions were observed with gene deletion mutations of CLA4 and BUD6 (AIP3). Cla4 is a PAK-like kinase involved in actin patch assembly and the cell cycle-dependent transition from apical to isotropic bud growth; Bud6 forms a complex with Bni1 and actin to control actin cable assembly and cell polarity. Tetrad analysis confirmed that both the bni1Δ bnr1Δ and bni1Δ cla4Δ double-mutants were inviable and that the bni1Δ bud6Δ double-mutant was associated with a slower growth rate or "synthetic sick" phenotype, reflecting reduced fitness of the double-mutant relative to the respective single mutants (FIG. 2B). This example thus demonstrates that the replica pinning procedure can identify genetic interactions corresponding to the spectrum of fitness defects from synthetic sick to synthetic lethal phenotypes.

Example 8

Input Array of 5,000 Strains Crossed with Uncharacterized Query Mutation

If synthetic lethal/sick interactions identify functionally related genes, then some of the uncharacterized genes identified in the bni1Δ screen should also participate in cortical actin assembly and cell polarity. To test this possibility, we conducted synthetic lethal/sick screen for a previously uncharacterized gene, BBC1. The bbc1Δ deletion mutant shows no obvious phenotype and the Bbc1 amino acid sequence is not indicative of a cellular role; however, Bbc1 contains an SH3 protein-protein interaction domain, suggesting that Bbc1 may function as part of a complex. We scored 16 potential synthetic lethal/fitness interactions for bbc1Δ, the majority of which have YPD-classified cell polarity or cell structure (cytoskeletal) roles (Table 1). In particular, bbc1Δ showed interactions with several genes whose products control actin polymerization and localize to cortical actin patches (CAP1, CAP2, SAC6, and SLA1), suggesting BBC1 may be involved in the assembly actin patches or their dependent processes. The results of additional experiments demonstrated that Bbc1 localized predominantly to cortical actin patches and that its SH3 domain binds directly to Las17 (Bee1), a member of the WASP (Wiskott-Aldrich syndrome protein) family proteins that controls the assembly of cortical actin patches through regulation of the Arp2/3 actin nucleation complex.

Example 9

Input Array of 5,000 Strains Crossed with Helicase Mutation

To explore the potential for the synthetic genetic analysis of the present invention to identify interactions for genes with roles distinct from cytoskeletal organization and cell polarity, we undertook screens with two non-essential genes that function in DNA damage and repair pathways. SGS1 encodes the yeast homolog of the human Werner's Syndrome protein, WRN, a member of the RecQ family of DNA helicases, while RAD27 encodes an enzyme that processes Okazaki fragments during DNA synthesis and repair. The phenotype of yeast cells deleted for the SGS1 gene mirrors the chromosomal instabilities and premature aging associated with Werner's syndrome. SGS1 is known to show a synthetic lethal/sick relationship with YNL218W, which encodes the yeast homolog of human Werner helicase interacting protein, and seven other genes (SLX1, MMS4, SLX3, SLX4, HEX3, HRP5, and SLX8), which are thought to mediate the resolution of recombination intermediates generated in the absence of SGS1. In total, we scored 24 potential synthetic lethal/fitness interactions for SGS1, the majority of which were associated with cellular roles in DNA synthesis and repair (Table 1). We identified 6 of the previously known synthetic lethal/sick interactions; the 2 that were missed (HEX3, SLX8) had severe growth defects that precluded propagation through the multiple pinning steps. Several novel SGS1 synthetic lethal/sick interactions are of considerable interest: RRM3, a gene that encodes a closely related helicase involved in rDNA replication; WSS1, a gene identified as a high dosage suppressor of SMT3, which codes a conserved ubiquitin-related protein that interacts with HEX3 in the two-hybrid system; YBR094W, a highly conserved gene of unknown function with an NH2-terminal SurE domain and COOH-terminal tubulin-tyrosine ligase-like domain; and ESC4, which codes for an uncharacterized gene with 3 BRCT domains, peptide recognition modules that appear to be found exclusively in proteins involved in DNA synthesis and repair.

Example 10

Network of Synthetic Lethal Analysis

Because many of the synthetic lethal/sick relationships appear to involve functionally related genes, the data set derived from large-scale synthetic genetic interactions should form a highly connected network in which genes are classified base upon their connectivities. To build a network of interactions and further explore the potential of this methodology, we conducted additional synthetic lethal/sick screens with specific query mutations in the following genes:

(i) bim1Δ, a complete deletion of BIM1, whose product localizes to the tips of astral microtubules and controls the orientation of the mitotic spindle.

(ii) nbp2Δ, a complete deletion of NBP2, gene of uncharacterized function that showed a synthetic lethal/sick interaction with BNI1; the Nbp2 product contains an SH3 domain and shows a two-hybrid interaction with Nap1.

(iii) arc40-1, a temperature sensitive allele of ARC40, an essential gene that codes for a component of the Arp2/3 complex, a seven-member complex that functions to nucleate actin filaments, controlling the assembly, movement, and localization of cortical actin patches in yeast.

(iv) arp2-2, a temperature sensitive allele of ARP2, coding for one of the key actin-related proteins of the Arp2/3 complex.

(v) rad27Δ, a complete deletion of RAD27, which showed a synthetic lethal/sick interaction with SGS1 and whose product functions as a nuclease that processes Okazaki fragments during DNA synthesis.

To plot the resultant synthetic lethal/sick interactions as a network, the data set was first imported into the Biomolecular Interaction Network Database (BIND), then formatted with BIND tools and exported to the Pajek package, a program originally designed for the analysis of social networks. The genetic interaction network shown in FIG. 3 contains 205 genes, represented as nodes on the graph, 292 synthetic lethal/sick interactions, represented as edges connecting genes. All of these interactions were first identified using the automated methodology and then confirmed by tetrad analysis. To visualize sets of genes with related functions, we color-coded the genes according to their YPD cellular roles and aligned the genes based upon both their roles and connectivity. These relationships can also be represented by two-dimensional hierarchical clustering, as is used for analysis of DNA microarray experiments. For genetic interaction data, both the query genes and the interacting genes are clustered based upon the similarity of their patterns of genetic interactions (FIG. 4).

Each of the query genes were biased towards interactions with genes of particular cellular roles. Moreover, subsets of interacting genes with the same cellular roles could distinguished from one another by their connectivity. For example, the BIM1 screen identified a large group of genes involved in mitosis (red genes), which include several components of the Bub2p- and Mad2p-dependent spindle assembly checkpoints (BUB1, BUB2, BUB3, BFA1, MAD1, MAD2, and MAD3) and multiple genes involved nuclear migration and spindle orientation during mitosis (BIK1, MCK1, SLK19, KIP3, PAC11, PAC1, NUM1, DYN1, JNM1, ARP1, ASE1), a subset of which also interacted with BNI1 and function specifically as part of the Dyn1 kinesin pathway. In addition, BIM1 interacted with a group genes that have a chromatin/chromosome structure cellular role (yellow genes), many of which have been implicated kinetichore function (CTF8, CTF19, MCM21, MCM22, and CHL4), and a total of 15 genes of with unknown cellular roles (black genes). To examine one of these uncharacterized genes in more detail, we conducted an NBP2 screen, which showed interactions with several genes involved in nuclear migration and spindle function (KAR9, CIN2 and KIP3), actin assembly (CAP1 and CAP2), and de novo folding of actin and tubulin (PAC10 and GIM5), suggestive of a general role in cytoskeletal organization.

The RAD27 screen resulted in 35 interactions, the majority of which occurred for genes with DNA synthesis/repair cellular roles (FIG. 3 green genes). The unprocessed Okazaki fragments of rad27Δ cells are probably recognized as nicks or converted into double-strand breaks as evidenced by a large set of previously known synthetic lethal/sick interactions with the genes encoding multiple components of the recombinational repair apparatus (RAD50, RAD51, RAD52, RAD54, RAD55, RAD57, MRE11, XRS2) and the DNA damage checkpoint signaling pathway (RAD9, RAD17, RAD24, DDC1). Intriguingly, we observed novel interactions with HST1 and HST2, two genes encoding Sir3-like deacetylases and CAC2, a gene coding for a chaperone that delivers acetylated histones to newly synthesized DNA, which may be indicative of a functional relationship amongst the products of these genes in chromatin assembly or silencing. RAD27 also showed a synthetic lethal/fitness with the SOD1 superoxide dismutase gene, and its copper chaperone, LYS7, suggesting that the antioxidant functions of Sod1 are required to protect the rad27Δ cells from accumulated DNA damage. Finally, RAD27 interacted with 4 genes of unknown function, for which we predict a possible role in a DNA synthesis and/or repair.

We scored 40 synthetic lethal/sick interactions for arc40-1, most of which have cell polarity or cell wall maintenance roles (Table 1), including 2 genes involved in Arp2/3 activation (VRP1 and MYO5). From a similar screen with a temperature sensitive ARP2 allele, arp2-1, we scored a total of 43 synthetic lethal/sick interactions. Strikingly, the ARP2 screen identified a large subset of 32 interactions that were shared with ARC40. Both screens identified a relatively small number of unique interactions, which included genes implicated in actin patch assembly (MYO5 with arc40-1 but not arp2-1; ARC18 and PRK1 with arp2-1 but not arc40-1) and may reflect roles specific to each Arp2/3 subunit. These findings suggest that genes whose products form functional complexes will show a highly similar but unique set of genetic interactions.

Example 11

Plasmid-Borne Approaches

The pinning procedure described for the construction of double mutants provides a simple method to move a plasmid of interest into the set of approximately 5,000 viable xxxΔ::KAN deletion mutants. In this procedure, the Y2454 starting strain is transformed with a URA3- or LEU2-based plasmid and then crossed into the haploid mutants by following steps 1–6 of the pinning procedure as described in Example 1 for genome-wide double-mutant construction. The ability to undertake plasmid-based screens with the complete deletion set greatly extends the number of possible genome-wide screens including synthetic dosage lethality and green-fluorescence protein-based reporter screens.

Example 12

Synthetic Lethal/Fitness Analysis Via Bar-coded Deletion Mutants and DNA Microarray Technology Genetic interactions for yeast mutant strains that contain "bar codes" for identification can be analyzed using DNA microarrays.

Step 1. The pool of MATαxxxΔ::KAN cells, containing the entire set of approximately 5,000 viable deletion mutants, will be mated to a Y2454-derivative for synthetic lethal analysis with a mutant allele marked with NAT (e.g. Y2454 made bni1Δ::NAT).

Step 2. The resultant pool of diploid cells is transferred to sporulation medium and MATa can1Δ MFA1-HIS3 cells are selected on synthetic medium that contains canavanine but lacks histidine.

Step 3. The pool of haploid MATa can1Δ MFA1-HIS3 cells are grown on medium containing geneticin to select for AMTa can1Δ MFA1-HIS3 xxxΔ::KANdeletion mutants Step 4. The MATa can1Δ MFA1-HIS3 xxxΔ::KAN cells are split into two samples. To determine the set of mutant cells that mated and sporulated efficiently, DNA will be prepared from one sample and used to probe the bar-coded microarray. DNA preparation of the DNA involves isolating genomic DNA and preparing bar code probes via a PCR-based method.

Step 5. To determine the set of synthetic lethal double mutants, the other sample of cells will first be grown on medium containing nourseothricin, which selects for double-mutant cells, e.g. MATa bni1Δ::LEU2 xxxΔ::KANR can1Δ MFA1-HIS3 cells. Then, DNA will prepared for bar-coded microarray analysis. Comparison of the bar-coded mutants that are present in sample 1 but not present in sample 2 identifies potential synthetic-lethal combinations.

Example 13

Synthetic Genetic Array Mapping (SGAM)

Mapping a Common Suppressor of Lethality Associated with cbk1Δ, mob2Δ, tao3Δ, hym1Δ, and kic1Δ Deletion Mutations:

The SGAM method was applied to study the Cbk1 signaling pathway. Deletion of CBK1, MOB2, HYM1, KIC1 or TAO3 genes in the S288c genetic background, in which the complete set of yeast deletion strains stains is constructed, is lethal, whereas the equivalent deletion in the W303 background is not. Tetrad analysis of crosses between the viable W303 deletion mutants and an S288c strain revealed that 50% of the spores carrying a deletion mutation would germinate to form a colony, indicating that a single W303-based suppressor allele rescued the lethality of each deletion. To map the suppressor allele, we first created appropriate starting strains for SGA analysis by crossing W303 strains that carried URA3 or natR marked deletions of the CBK1, MOB2, HYM1, KIC1, and TAO3 with an S288c strain that carried the SGA mating type specific haploid selection reporters (can1Δ::MFA1pr-HIS3::MFα1pr-LEU2). SGA analysis was carried out with cbk1Δ, mob2Δ, hym1Δ, kic1Δ, and toa3Δ as query mutations against ~4700 viable xxxΔ::kanR deletion strains and colony growth defects in the resultant double deletion meiotic progeny were scored. We performed the strain manipulation robotically; however, SGA analysis can also be conducted by hand pinning.

Because it was likely that a single W303-derived suppressor mutation rescued the lethality of each deletion, we pooled the resultant genetic interactions and examined those that occurred for at least four of the five Cbk1 pathway deletions. In total, 31 deletions interacted with all five of the pathway members and 85 deletions interacted with four of the pathway members (see Supplementary Table for results of all screens). We designed an algorithm (discussed herein) to identify chromosomal regions that were enriched in genetic interactions. For a single colinear set of 48 genes, spanning an 89.6 kb region (~28 cM) of chromosome IV (MAPS), we identified 13 genetic interactions, which represents a statistically significant enrichment (FIGS. 6, 7) and presumably mapped the location of the W303-derived suppressor. This same region could also be identified from the primary data collected for three of the individual screens (hym1Δ, kic1Δ and tao3Δ, see FIG. 7), but pooling the data from all five screens provides a method for removing false positives associated with the high throughput analysis.

Figure 7:
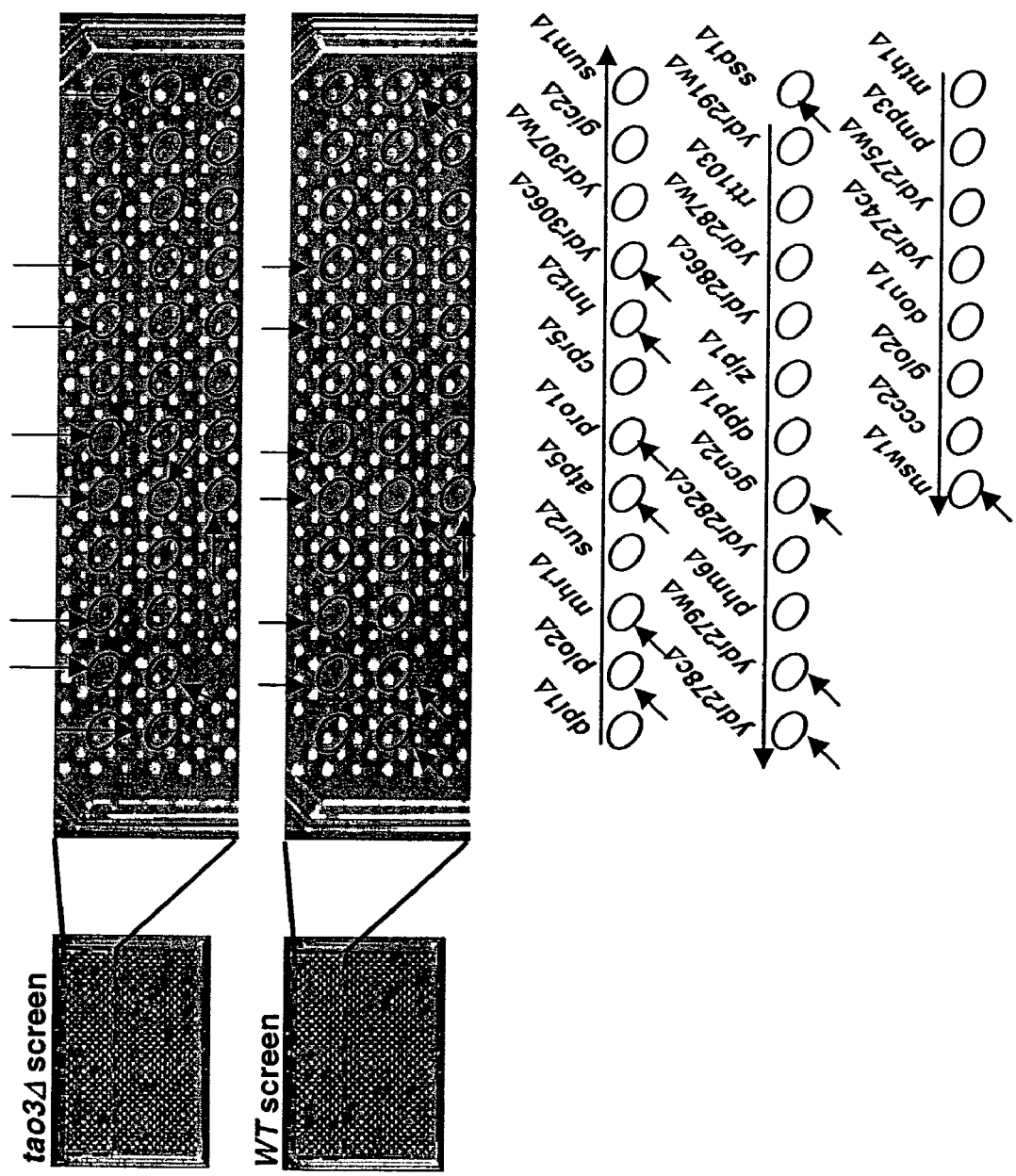
FIG. 7 demonstrates that a linked region of inviable or slow growing double mutants surrounds the SSD1 locus when SGA analysis is carried out with deletions of Cbk1 signaling pathway components. In the final step of SGA analysis, double mutant progeny are selected by growth on SD his- arg- ura- plates supplemented with L-canavanine and G418 (see below). One of the 16 plates of arrayed double mutant progeny contained the ssd1Δ::kanR strain and most of the deletions surrounding the SSD1 locus in the top half of the plate (dotted lines); this plate and region are shown for a wild type control screen (Y2806) and a tao3Δ:: URA3 (Y3714) screen. Each deletion strain is represented twice on the plate, located immediately diagonal to one another. In almost all cases, the size of the two colonies is identical, although there are exceptions (e.g. only one of the ssd1Δ::kanR colonies grew up in the tao3Δ::natR screen). The ssd1Δ::kanR strain and deletions linked to the SSD1 locus are outlined; circles with no arrows indicates tao3Δ:: URA3 xxxΔ::kanR double deletions (top panel) that showed reduced colony size relative to the xxxΔ::kanR deletion alone (wild type control screen, middle panel) while circles with arrows indicates roughly equal colony size in the two screens. The presence of circles with arrows, indicating equal growth in the presence and absence of TAO3, in the middle of the linked group of synthetic genetic interactions (circles with no arrows), can be explained by: i) growth defects, even in the presence of TAO3 (e.g. gcn2Δ, atp5Δ), which prevent the synthetic genetic interaction from being observable (see FIG. 6 legend), and ii) weak or uncertain interactions (e.g. hnt2Δ). The identities of each of the xxxΔ::kanR deletions is shown in the bottom panel. The deletion strains are arrayed on the plates in the same order as the corresponding genes on Chromosome IV, arrows indicate the topology of the genes with respect to the SSD1 locus, with the arrowhead pointing away from the SSD1 locus. Because
Figure 8:
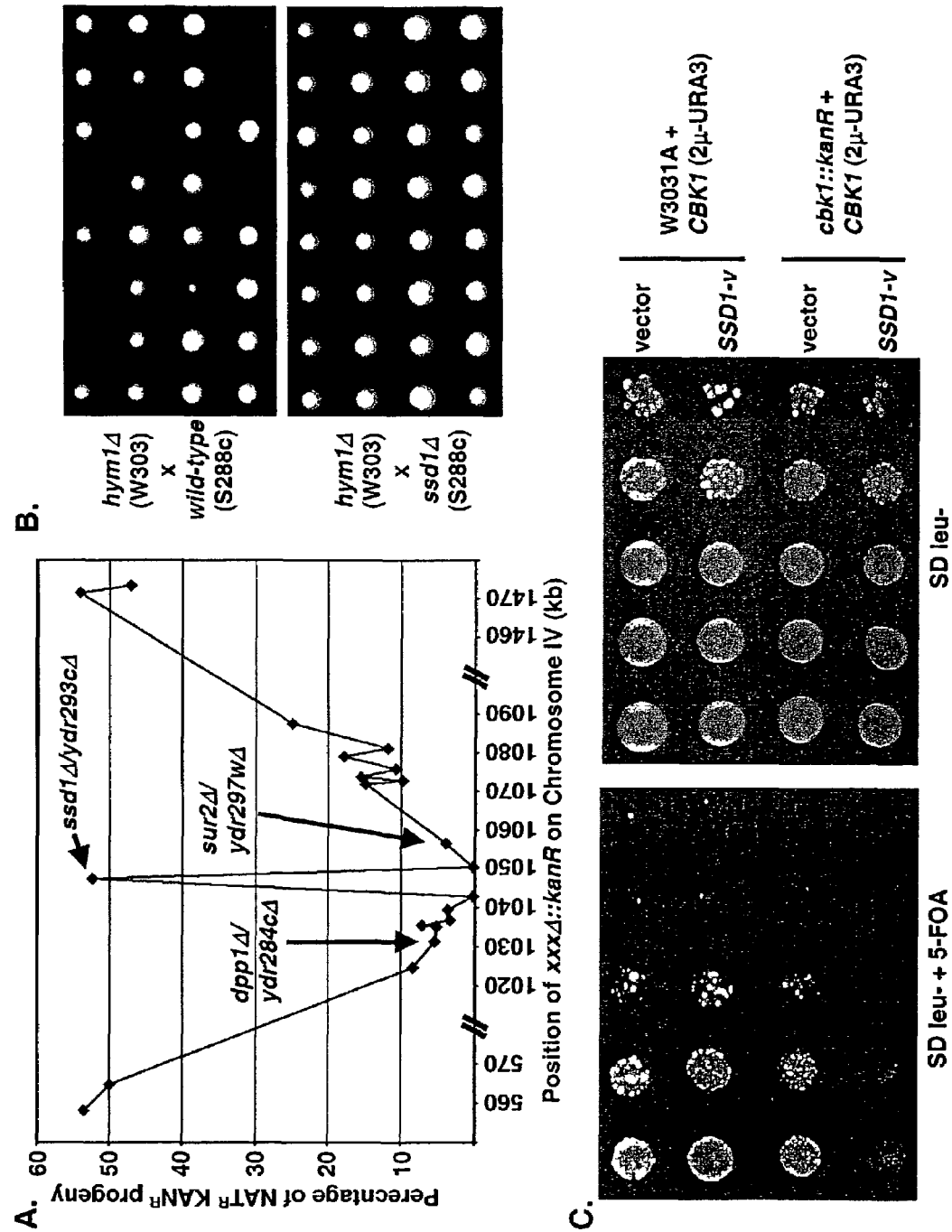
FIG. 8A shows that mutations in SSD1 suppress the lethality associated with deletion of genes coding for Cbk1 pathway components. (A) Random spore analysis was carried out as described below to determine the percent recombination between the W303-specific suppressor of mob2Δ:: natR and kanR-marked deletions on a section of chromosome IV in the vicinity of the SSD1/YDR293C locus. The percent recombination was plotted vs. position on chromosome IV, with the end of the ORF closest to the central SSD1 locus determining the plotted base pair. As kanR-marked deletions approached SSD1, the percentage of recombinant progeny approached zero. At loci far removed from SSD1, the percent recombination returned to ~50%. The ~50% recombination seen for ssd1Δ::kanR is actually due to suppression of the lethality associated with mob2Δ:: natR by ssd1Δ::kanR.
FIG. 8B indicates how tetrad analysis confirmed that ssd1Δ::kanR suppresses the lethality associated with deletion of HYM1. When a viable W303-derived hym1Δ:: URA3 is crossed to a wild type S288c strain, a single suppressor segregates with viability of the hym1Δ:: URA3, i.e. 50% of the hym1Δ:: URA3 spores (25% of all spores) germinate to form a colony (top panel). When the W303-derived hym1Δ::URA3 was crossed to an S288c-derived ssd1Δ::kanR strain, all hym1Δ::URA3 spores were viable (bottom panel), indicating that the W303-derived suppressor of the lethality associated with hym1Δ::URA3 is tightly linked to ssd1Δ::kanR, which also suppresses the hym1Δ-associated lethality. Identical results were obtained for cbk1Δ, mob2Δ, tao3Δ and kic1Δ.
FIG. 8C demonstrates that when expressed in the W303 background, SSD1-v rescued the inviability normally associated with CBK1 deletion. Congenic wild-type and cbk1Δ strains were sequentially transformed with a URA3-marked YEp24 plasmid containing the CBK1 gene (P3765) and either a LEU2-marked YEp13 plasmid carrying SSD1-v (MTP251) or the YEp13 empty vector. These strains were grown to saturation in SD leu- ura-, serially diluted (four 10-fold dilutions), and then culture and each dilution were spotted on SD leu- and SD leu-containing 5-FOA, a drug which is toxic to yeast expressing the URA3 gene. In the presence of SSD1-v, the cbk1Δ strain could not form colonies on SD leu- containing 5-FOA and, therefore, could not lose the URA3-marked plasmid containing the CBK1 gene.

Mutations in SSD1 Restore Viability to Strains Defective in Cbk1 Pathway Signaling:

Random spore analysis enabled us to determine the frequency of recombination between the putative Cbk1 pathway suppressor and the kanR marked deletion alleles in the region. The mob2Δ::natR SGA starting strain (Y3968) was mated to each deletion strain in this linked region. Viable MATa mob2Δ::natR meiotic progeny were selected for and replica plated onto media containing G418 to determine the percent of viable MATa mob2Δ::natR xxxΔ::kanR recombinants (FIG. 8A). For gene deletions such as dpp1Δ/ydr284cΔ and sur2Δ/ydr297wΔ, <10% of the viable MATa mob2Δ::natR meiotic progeny would also grow on the G418 medium, as expected if a W303-based suppressor was linked to these deletion alleles (FIG. 5). In contrast, for ssd1Δ::kanR, ~50% of the viable MATa mob2Δ::natR meiotic progeny also grew on the G418 medium, suggesting that ssd1Δ: :kanR suppresses the lethality associated with the mob2Δ::natR deletion. Indeed, unlike other deletions in this region, ssd1Δ::kanR showed no synthetic interactions with any of the Cbk1 pathway members by SGA analysis (FIGS. 6 and 7). Tetrad analysis confirmed that ssd1Δ::kanR suppressed the lethality associated with all five deletion strains, cbk1Δ, mob2Δ, hym1Δ, kic1Δ, and toa3Δ (FIG. 8B). These results suggest that the W303-derived suppressor of Cbk1 pathway deletions is either a hypomorphic or null allele of SSD1. SSD1 is a putative RNA binding protein implicated in the regulation of cell polarity and cell integrity whose gene product may physically interact with Cbk1 (RACKI et al. 2000 EMBO J. 19: 4524–32; HO et al. 2002 Nature 415: 180–3). It has been well established that SSD1 is polymorphic in laboratory strains of *S. cerevisiae*; most S288c strains carry the dominant SSD1-v allele, while W303 harbors the recessive ssd1-d allele (SUTTON et al. 1991 Mol. Cell. Biol. 11: 2133–48). Thus, the lethality associated with perturbation of Cbk1 pathway signaling can be suppressed by either the ssd1-d allele or the ssd1Δ deletion allele. We sequenced the ssd1-d allele in the W303 background and compared it to the SSD1-v allele sequenced as part of the yeast genome project (GOFFEAU et al. 1996 Science 274: 546, 563–7). A point mutation at base pair 2094 (C to G) of the SSD1 open reading frame creates a premature stop codon in the W303 ssd1-d, resulting in a truncated protein with a predicted molecular weight of ~77 kDa. These findings are consistent with the observation that ssd1-d is expressed as a truncated ~83 kDa protein (UESONO et al. 1997 J. Biol. Chem. 272: 16103–9). While this work was in progress, Du and Novick identified mutations in SSD1 as suppressors of cbk1Δ and tao3Δ, by a transposon insertion mutagenesis approach (DU and NOVICK 2002 Mol. Biol. Cell 13: 503–14).

To confirm that the SSD1-v allele present in the S288c genome is toxic to W303 strains lacking the Cbk1 signaling pathway, we used a plasmid loss assay. cbk1Δ and congenic wild-type cells (W303 background) were transformed with a plasmid containing the CBK1 gene and maintained with the URA3 selectable marker. The plasmid rescued several cbk1Δ phenotypes (see below). These strains were then transformed with either a LEU2-marked plasmid housing the SSD1-v allele or the empty vector. The four Ura+ Leu+ genetic combinations were cultured and plated on SD leu- and SD leu- containing 5-FOA. On both types of plates, the absence of leucine maintained the LEU2-marked plasmids, but on the plates containing 5-FOA, cells possessing URA3-marked plasmids were selected against. In wild-type transformants, in either the presence or absence of SSD1-v, some of the plated cells formed colonies on SD leu- containing 5-FOA as these cells could grow in the absence of the the URA3-marked plasmid (FIG. 8C). Further, cbk1Δ cells transformed with the LEU2-marked empty vector formed colonies on SD leu-containing 5-FOA. However, cbk1Δ cells transformed with the LEU2-marked vector housing SSD1-v did not form colonies on SD leu- media containing 5-FOA (FIG. 8C), indicating that in the presence of SSD1-v, cells lacking CBK1 (carried by the URA3 plasmid) were not viable. When introduced into the W303 background, the SSD1-v allele rescued the inviability normally associated with CBK1 deletions.

Synthetic Lethality with Genes Encoding Cbk1 Pathway Components:

The SGA screens used for mapping the Cbk1 pathway suppressor also provided many candidate synthetic genetic interactions at loci unlinked to SSD1 (FIG. 6A). Here, we directly examined a subset of the strongest synthetic genetic interactions. Tetrad analysis confirmed that 9 deletions unlinked to SSD1 are important for growth in haploid cbk1Δ:: URA3 ssd1-d cells and hym1Δ::URA3 ssd1-d cells (Table 2B). Four of these genes are involved in reorganization of the cortical actin cytoskeleton (BEM1, BEM2, BEM4, SAC7) and play key roles in bud emergence and development. Another gene, NBP2, has been generally implicated in cytoskeletal organization because nbp2Δ is synthetically lethal with several genes involved in spindle orientation and actin assembly (TONG et al. 2001 Science 294: 2364–2368). Moreover, the Nbp2 ortholog in fission yeast, Skb5, appears to bind and activate the PAK-like kinase Shk1 (YANG et al. 1999 J. Biol. Chem. 274: 36052–7) and shk1Δ shows synthetic lethality with a deletion of the gene encoding the Cbk1 ortholog, Orb6 (VERDE et al. 1998 Proc. Natl. Acad. Sci. USA 95: 7526–31). Two other genes (GAS1, KRE1) are directly involved in cell wall maintenance through beta-1,6-glucan crosslinking and assembly. Finally, two of the genes (BST1, GOS1) are involved in vesicular transport. All of these genes function directly or indirectly in polarized cell growth, which could explain their essential role in ssd1-d cells defective for Cbk1 pathway signaling.

Ordered Arrays as Mapping Tools:

Ordered arrays of the marked yeast deletion strains provide an inherently powerful tool for high resolution genetic mapping. When combined with SGA methodology, this mapping method can be automated and carried out in high throughput. Although the test case shown here demonstrated mapping the suppressor of an essential gene deletion mutation, SGAM can be applied to any allele that leads to an epistatic phenotype that S288c strains do not normally display. These phenotypes include suppression of conditional alleles of essential genes, cytotoxic drug resistance and filamentous growth. SGAM may be of particular use for rapid mapping of dominant mutations, which can be challenging to clone with standard techniques. Furthermore, we expect that the rapid exploration of all null phenotypes, as allowed by the yeast deletion sets, will eventually lead researchers to a fuller exploration of genetic space, as provided by screens for dominant alleles. In theory, several alleles responsible for complex, multigenic quantitative traits, such as the high temperature growth phenotype of pathogenic *S. cerevisiae*, could be mapped in a single round of SGA analysis (MCCUSKER et al. 1994 Genetics 136: 1261–9; STEINMETZ et al. 2002 Nature 416: 326–330). To further enable the mapping process, the unique oligonucleotide bar code tags built into each yeast deletion strain may be exploited for quantitative analysis of growth phenotypes of meiotic progeny by hybridization to DNA microarrays (SHOEMAKER et al. 1996 Nat. Genet. 14: 450–6).

Other methods for rapid mapping of mutations have been devised. For instance, thousands of markers provided by the allelic variation between different strains of *S. cerevisiae* have been detected with high-density oligonucleotide arrays and exploited for mapping novel mutations (WINZELER et al. 1998 Science 285: 901–6). When the mutant phenotype is amenable (see above), mapping with SGA analysis may be preferable to mapping with oligonucleotide arrays because of the potential for higher resolution. In the first stage of SGA mapping, a starting strain is crossed to ~4700 deletion stains to identify a chromosomal region(s) centered around the mutation. In the example presented here, a 89.6 kb (~28 cM) region was detected (FIG. 6). This mapping resolution is similar to that obtained in test applications of high-density oligonucleotide arrays (WINZELER et al. 1998), which detected 11 to 64 kb regions surrounding 4 known loci. However, in the second stage of SGA mapping, random spore analysis of the meiotic progeny derived from deletion strains in the identified chromosomal region pinpoints the gene(s) tightly linked to the mutation. While S. cerevisiae genetics is particularly suited for automation and large-scale genetic analysis, the construction of ordered arrays of gene deletion mutants would enable this type of approach to be applied to other model organisms.

Yeast Strains and Media:

Yeast strains used in this study are listed in Table 2A. S288c-derived strains are congenic with BY4741 (BRACHMANN et al. 1998), except at indicated loci. W303-derived strains are congenic with W3031A (HIRSCH et al. 1991), except at the indicated loci. YPD is 2% peptone, 1% yeast extract, 2% glucose and 2% agar. Sporulation media is 2% agar, 1% potassium acetate, 0.1% yeast extract, 0.05% glucose, supplemented with uracil, histidine, and leucine. SD media is 0.2% amino acid drop out mix, 0.17% yeast nitrogen base without amino acids and ammonium sulphate, 0.5% ammonium sulphate, 2% glucose, and 2% agar. Filter sterilized solutions of L-canavanine (Sigma, 50 mg/L), G418 (Gibco-BRL, 200 mg/L) and clonNAT (Werner Bioagents, 100 mg/L) were added to cooled (<50° C.), autoclaved media where indicated. In cases where SD media was supplemented with clonNAT or G418, the ammonium sulphate was replaced with 0.1% monosodium glutamate.

SGA Analysis:

SGA analysis was carried out as described in the preceeding examples. Starting strains for SGA analysis were generated following two backcrosses of the viable W303-derived deletions, cbk1Δ::URA3 (Y3576), hym1Δ::URA3 (Y1560), mob2Δ::natR (Y3732), kic1Δ::URA3 (Y3400), or tao3Δ::URA3 (Y3577), to S288c-derived strains. First, the deletion mutants were crossed to Y3068 (MATα can1Δ::MFA1pr-HIS3::MFα1pr-LEU2 ura3Δ0 leu2Δ0 his3Δ1 lys2Δ0) and MATa can1Δ::MFA1pr-HIS3 progeny carrying the URA3- or natR-marked deletion alleles were isolated by tetrad dissection. These strains were then mated to Y3655 (MATα can1Δ::MFA1pr-HIS3::MFα1pr-LEU2 ura3Δ0 leu2Δ0 his3Δ1 lys2Δ0) and MATa can1Δ::MFA1pr-HIS3::MFα1pr-LEU2 progeny carrying the URA3- or natR-marked deletions were obtained by tetrad analysis. Tetrad analysis revealed that 50% of the cbk1Δ, hym1Δ, mob2Δ, kic1Δ, or tao3Δ deletion mutants were viable suggesting that a single suppressor allele segregated in the crosses and rescued the lethality associated with each deletion. For SGA analysis, MATα starting strains, cbk1Δ::URA3 (Y3717), hym1Δ::URA3 (Y3716), mob2Δ::natR (Y3968), kic1Δ::URA3 (Y3715), or tao3Δ::URA3 (Y3714) were mated to ~4700 individual MATa xxxΔ::kanR S288c haploid deletion strains. Yeast arrays were manipulated with a CPCA robot (Virtek/ESI, Toronto). Diploids were selected on SD ura-lys-plates or YPD plates supplemented with G418 and clonNAT for 1 day at 30° C. and then sporulated for 5 days at room temperature. To select for MATa can1Δ::MFA1pr-HIS3::MFα1pr-LEU2 meiotic progeny, spores were germinated on SD his-arg-media supplemented with L-canavanine for 2 days at 30° C., then transferred onto a fresh plate of the same media for a further day of growth at 30° C. The resultant colonies were then transferred to SD his-arg-supplemented with L-canavanine and G418 to select for MATa xxxΔ::kanR meiotic progeny. Finally, cells were transferred to either SD his-arg-ura-supplemented with L-canavanine and G418 or to SD his- arg- supplemented with L-canavanine, G418, and clonNAT, to select for MATa double mutant meiotic progeny. SGA analysis was carried out 3 times on each starting strain and a synthetic interaction was scored if a gene deletion was synthetic lethal/sick in 1 or more of the 3 screens.

To confirm some of the synthetic genetic relationships between the Cbk1 pathway deletions and gene deletions unlinked to SSD1, 31 deletions that appeared synthetic lethal in 5 out of 5 screens were mated to the cbk1Δ::URA3 (Y3576) and hym1Δ::URA3 (Y1560) starting strains and subjected to tetrad analysis. A subset of 17 deletions that showed synthetic interactions in 4 out of 5 screens and had known or suspected roles in cell polarity or structure were also subjected to tetrad analysis with cbk1Δ::URA3 and hym1Δ::URA3. Spores were separated and germinated on YPD media. 9 out of the 48 (19%) interactions observed by SGA analysis that were not linked to SSD1/YDR293C could be confirmed by tetrad analysis. The relatively high false positive rate may be due in part to the large number of loci (5) that must segregate to generate viable Nat$^R$ (or Ura$^+$) Kan$^R$ meiotic progeny and/or the sporulation defect associated with abrogation of the Cbk1 signaling pathway.

Algorithm for Detecting Significant Groups of Linked Genetic Interactions in SGA Data:

A list of gene deletions that were synthetic lethal/sick with at least 4 of the 5 Cbk1 pathway deletions was queried versus the list of ~4700 kanR-marked deletion mutants contained in our arrays. First, the marginal probability ($p_m$) of a synthetic interaction was calculated from the total number of interactions divided by the total number of deletion strains screened. At each gene represented by a deletion strain, the number of synthetic interactions in the region surrounding that gene (5 deletions in each direction) was calculated. The probability of observing this many interactions by chance alone was determined from a binomial distribution, assuming the probability of an interaction at any given gene is $P_m$. A Bonferroni correction was employed to account for multiple comparisons.

Random Spore Analysis:

21 strains deleted for genes surrounding SSD1, for SSD1 itself, and for four ORFS lying at a great distance from SSD1 on chromosome IV were mated to the mob2Δ::natR (Y3968) starting strain for SGA analysis. The heterozygotes were sporulated for 10+ days at room temperature and subjected to random spore analysis. Spores were released from asci by a 30 min incubation at 30° C. with 0.6mg/mL zymolyase in 1M sorbitol, followed by 1 min of vigorous vortexing. The separated spores were diluted in distilled water and spread on 2 SD-his-arg+L-canavanine+clonNAT plates to select for germination of MATa can1Δ::MFA1pr-HIS3::MFα1pr-LEU2 mob2Δ::natR spores. Plates were incubated at 30° C. for 3 days. 50–400 colonies were obtained per plate for each strain. Each plate was replicated onto SD-his-arg+L-canavanine+clonNAT+G418 and incubated for 2 days at 30° C. to determine what percent of viable MATa mob2Δ::natR spore colonies were Kan$^R$.

Sequencing:

A ~4kb fragment containing the entire SSD1 open reading frame, as denoted in the Saccharomyces Genome Database (SGD), was amplified by PCR with the Expand Long Template PCR System (Roche) using the primers oMT1183/SSD1-UP (5' GTCACTTTAATATCGCAAAACAG; SEQ ID NO: 1) and oMT1182/SSD1-DOWN (5' GGATACT-GAGGGGTGAAGC; SEQ ID NO: 2). Fifteen individual PCR reactions were pooled, the fragment purified with a Qiaquick PCR Purification Kit (Qiagen), and the coding strand sequenced (ACGT Corporation). No mutations were detected in bp 1–2093 of the SSD1 open reading frame. A single base pair change was detected at nucleotide 2094, a C (SGD) to G (W303) mutation, that creates a premature stop codon resulting in a truncated protein with a predicted molecular weight of ~77kDa. An identical mutation was found in the ssd1-d allele of a S288C-derived strain, JO371.

Rescue of cbk1Δ Inviability in the W303 Background by SSD1-v:

cbk1Δ::kanR (Y1748) and congenic wild-type (W303 1A) strains in the W303 genetic background were transformed with plasmid P3765, a derivative of YEp24 (2μ, URA3) that houses a genomic fragment containing the CBK1 gene. P3765 rescues both the "crusty" colony and cell clumping phenotypes of Y1748. Individual Ura+ transformants were subsequently transformed with either plasmid YEp13 (2μ, LEU2) or plasmid MTP251, a derivative of YEp13 that houses a genomic fragment containing SSD1-v. Three Ura+ Leu+ transformants were picked and inoculated into SD ura- leu- and grown to saturation at 30° C. Cultures were serially diluted (four 10-fold dilutions) in SD ura-leu- then 5 μL of culture and each dilution was spotted onto SD leu- and SD leu-containing 0.1% 5-fluoro-orotic acid (5-FOA). Plates were photographed after 2 days at 30° C.

TABLE 2A

Yeast Strains

| Strain Name | Background | Relevant Genotype | Source |
|---|---|---|---|
| W3031A | W303 | MATa ura3-1 leu2-3,112 his3-11 15 trp1-1 ade2-1 can1-100 | J. Hirsch |
| Y3576 | W303 | W3031A cbk1Δ::URA3 | This study |
| Y1560 | W303 | W3031A hym1Δ::URA3 | This study |
| Y3732 | W303 | W3031A mob2Δ::natR | This study |
| Y3400 | W303 | W3031A kic1Δ::URA3 | This study |
| Y3577 | W303 | W3031A tao3Δ::URA3 | This study |
| Y1748 | W303 | W3031A MATα cbk1::kanR | This study |
| BY4741 | S288c | MATa his3Δ1 leu2Δ0 ura3Δ0 met15Δ0 | BRACHMANN et al. (1998) Yeast 14:115–32 |
| Y3068 | S288c | MATα can1Δ::MFA1pr-HIS3 ura3Δ0 leu2Δ0 his3Δ1 lys2Δ0 | TONG et al. (2001) |
| Y3655 | S288c | MATα can1Δ::MFA1pr-HIS3::MFα1pr-LEU2 ura3Δ0 leu2Δ0 his3Δ1 lys2Δ0 | TONG et al. (2001) |
| Y2806 | S288c | MATα can1Δ::MFA1pr-HIS3 leu2Δ0 his3Δ1 lys2Δ0 | TONG et al. (2001) |
| Y3717 | W303/S288c hybrid | MATα can1Δ::MFA1pr-HIS3::MFα1pr-LEU2 ura3 leu2 his3 lys2 cbk1Δ::URA3 | This study |
| Y3716 | W303/S288c hybrid | MATα can1Δ::MFA1pr-HIS3::MFα1pr-LEU2 ura3 leu2 his3 lys2 hym1Δ::URA3 | This study |
| Y3968 | W303/S288c hybrid | MATα can1Δ::MFA1pr-HIS3::MFα1pr-LEU2 ura3 leu2 his3 lys2Δ0 mob2α::natR | This study |
| Y3715 | W303/S288c hybrid | MATα can1Δ::MFA1pr-HIS3::MFα1pr-LEU2 ura3 leu2 his3 lys2Δ0 kic1Δ::URA3 | This study |
| Y3714 | W303/S288c hybrid | MATα can1Δ::MFA1pr-HIS3::MFα1pr-LEU2 ura3 leu2 his3 lys2Δ0 tao3Δ::URA3 | This study |

TABLE 2B

Genes important for growth in the absence of the Cbk1 pathway signaling

| Gene Name | ORF | Functional Information |
|---|---|---|
| BEM1 | YBR200W | Bud site assembly and cell polarity, SH3-domain protein that binds Cdc24, Ste5, Ste20, Rsr1. |
| BEM2 | YER155C | Bud site assembly and cell polarity, member of the family of Rho-type GTPase-activating proteins. |
| BEM4 | YPL161C | Bud site assembly and cell polarity, interacts with several Rho-type GTPases. |
| BST1 | YFL025C | Vesicular transport, postulated to negatively regulate COPII vesicle formation. |
| GAS1 | YMR307W | Cell wall maintenance, regulates beta-1,6-glucan crosslinking, null mutant has cell separation defects. |
| GOS1 | YHL031C | Vesicular transport, SNARE protein in ER to Golgi docking complex. |
| KRE1 | YNL322C | Cell wall maintenance, needed for beta-1,6-glucan assembly. |
| NBP2 | YDR162C | Unknown function, has an SH3 domain. |
| SAC7 | YDR389W | Cell structure and actin assembly, GTPase-activating protein for Rho 1. |

Tetrad analysis confirmed that these genes are synthetic lethal or sick with cbk1Δ and hym1Δ. Gene functions were obtained from the Saccharomyces Genome Database and the Yeast Proteome Database.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for generating an output array of multiple diploid yeast strains, wherein each diploid yeast strain carries at least two genetic alterations relative to a starting yeast strain, and wherein the combination of the at least two genetic alterations is different in each diploid yeast strain, the method comprising:
- a) generating multiple derivative yeast strains from a starting yeast strain, each derivative yeast strain carrying a starting genetic alteration relative to the starting yeast strain and wherein at least one derivative yeast strain contains a recombinant construct comprising a mating type specific promoter operably linked to a selectable marker which permits efficient recovery of haploid spore progeny and permits selection of a particular haploid mating type;
- b) mating sets of two derivative yeast strains of step (a) to provide resulting diploid yeast strains, wherein each of the two derivative yeast strains mated contains a starting genetic alteration relative to the starting yeast strain, which starting genetic alteration is different in each of the two mated derivative yeast strains;
- c) recovering multiple resulting diploid yeast strains from the mating of step (b), wherein each resulting diploid yeast strain carries a resulting genetic alteration, said resulting genetic alteration comprising the starting genetic alterations from each of the two derivative yeast strains mated in step (b); and
- d) arraying the resulting diploid yeast strains recovered in step (c) carrying the resulting genetic alterations as a diploid output array, wherein the combination of the starting genetic alterations comprised by said resulting genetic alteration is different in each of the arrayed resulting diploid yeast strain.

2. A method for generating an output array of multiple haploid yeast strains, wherein each haploid yeast strain carries at least two genetic alterations relative to a starting yeast strain, and wherein the combination of the at least two resulting genetic alterations is different in each haploid yeast strain, the method comprising:
- a) generating multiple derivative yeast strains from a starting yeast strain, each derivative yeast strain carrying a starting genetic alteration relative to the starting yeast strain, and wherein at least one derivative yeast strain contains a recombinant construct comprising a mating type specific promoter operably linked to a selectable marker which permits the efficient recovery of haploid spore progeny and permits selection of a particular haploid mating type;
- b) mating sets of two derivative yeast strains of step (a), wherein each of the two derivative yeast strains mated contains a starting genetic alteration relative to the starting yeast strain, which starting genetic alteration is different in each of the two mated derivative yeast strains;
- c) causing the diploid progeny of the derivative yeast strains mated in step (b) to undergo sporulation to provide resulting haploid strains;
- d) germinating a single mating type from the resulting haploid strains produced in step (c);
- e) growing the resulting haploid yeast strains germinated in step (d) using selective growth criteria;
- f) recovering multiple resulting haploid yeast strains grown in step (e), wherein each resulting haploid yeast strain carries a resulting genetic alteration, said resulting genetic alteration comprising the starting genetic alterations from each of the two derivative yeast strains mated in step (b); and
- g) arraying the resulting haploid yeast strains recovered in step (f) carrying the resulting genetic alterations as an output array, wherein the combination of the starting genetic alterations comprised by said resulting genetic alteration is different in each arrayed resulting haploid yeast strain.

3. The method of claim 2, wherein the starting yeast strain is selected from any yeast species that has two mating types and is capable of meiotic and mitotic reproduction.

4. The method of claim 3, wherein the starting yeast strain is selected from either the *Saccharomyces cerevisiae* or the *Schizosaccharomyces pombe* species.

5. The method of claim 2, wherein the derivative yeast strains and arrayed resulting yeast strains are located on plates, with between about 90 and 6200 yeast colonies on one plate.

6. The method of claim 2, wherein a resulting haploid yeast strain is a double mutant, the double mutant comprising mutations of two different endogenous mutated yeast genes.

7. The method of claim 6, wherein the double mutant comprises a deletion of two different non-essential yeast genes.

8. The method of claim 6, wherein the double mutant is either a synthetic lethal double mutant or a synthetic fitness double mutant.

9. The method of claim 2, wherein the output array comprises between about 1,000 and about 25 million resulting haploid yeast strains.

10. The method of claim 2, wherein the starting genetic alteration in at least one derivative yeast strain is selected from the group consisting of: introduction of a gene coding for expression of an aptamer; introduction of a protein-protein interaction detection system; introduction and expression of a heterologous gene from a viral, prokaryotic, or eukaryotic genome, wherein said heterologous gene either has or does not have a yeast homolog; transfection with a promoter operably linked to a reporter gene; and mutation or deletion of an endogenous yeast gene.

11. The method of claim 10, wherein the starting genetic alteration in both derivative yeast strains is selected from the group consisting of: introduction of a gene coding for expression of an aptamer; introduction of a protein-protein interaction detection system; expression of a heterologous gene from a viral, prokaryotic, or eukaryotic genome, wherein said heterologous gene either has or does not have a yeast homolog; transfection with a promoter operably linked to a reporter gene; and mutation or deletion of an endogenous yeast gene.

12. The method of claim 10, wherein the aptamer is either a protein aptamer or a nucleic acid aptamer.

13. The method of claim 10, wherein the aptamer performs a function selected from the group consisting of inhibiting expression of a gene, increasing expression of a gene, inhibiting protein-protein interactions, enhancing protein-protein interactions, inhibiting an activity of a protein, and enhancing an activity of a protein.

14. The method of claim 10, wherein the protein-protein interaction detection system is selected from the group consisting of a yeast two-hybrid system, a Ras recruitment system, a split ubiquitin system, and a protein fragment complementation systems.

15. The method of claim 10, wherein the heterologous gene is a human gene.

16. The method of claim 15, wherein the human gene comprises a set of alleles, each differing by one or more SNPs (small nucleotide polymorphisms).

17. The method of claim 2, wherein robotic manipulation is utilized.

18. A method for conducting synthetic lethal analysis of yeast colonies within an array of multiple yeast strains, the method comprising:
   a) generating an output array of multiple resulting haploid yeast strains according to the method of claim 2;
   b) comparing growth and viability of the resulting haploid yeast strains arrayed in step g) of claim 2 to growth and viability of the derivative yeast strains mated in step b) of claim 2; and
   c) detecting which resulting haploid strains contain synthetic lethal resulting genetic alterations by observing differences in the growth and viability of the resulting haploid strains as compared to the growth and viability of the derivative yeast strains.

19. The method of claim 18, wherein the starting yeast strain is selected from any yeast species that has two mating types and is capable of meiotic and mitotic reproduction.

20. The method of claim 19 wherein the starting yeast strain is selected from either the *Saccharomyces cerevisiae* or the *Schizosaccharomyces pombe* species.

21. The method of claim 18, wherein the derivative yeast strains and arrayed resulting yeast strains are located on plates, with between about 90 and 6200 yeast colonies on one plate.

22. The method of claim 18, wherein a resulting haploid yeast strain is a double mutant, the double mutant comprising a mutation of two different endogenous yeast genes.

23. The method of claim 22, wherein the double mutant comprises a deletion of two different non-essential yeast genes.

24. The method of claim 22, wherein the double mutant is either a synthetic lethal double mutant or a synthetic fitness double mutant.

25. The method of claim 18, wherein the output array comprises between about 1,000 and about 25 million resulting haploid yeast strains.

26. The method of claim 18, wherein the starting genetic alteration in at least one derivative yeast strain is selected from the group consisting of: introduction of a gene coding for expression of an aptamer; introduction of a protein-protein interaction detection system; introduction and expression of a heterologous gene from a viral, prokaryotic, or eukaryotic genome, wherein said heterologous gene either has or does not have a yeast homolog; transfection with a promoter operably linked to a reporter gene; and mutation or deletion of an endogenous gene.

27. The method of claim 26, wherein the starting genetic alteration in both starting yeast strains is selected from the group consisting of: introduction of a gene coding for expression of an aptamer; introduction of a protein-protein interaction detection system; introduction and expression of a heterologous gene from a viral, prokaryotic, or eukaryotic genome, wherein said heterologous gene either has or does not have a yeast homolog; transfection with a promoter operably linked to a reporter gene; and mutation or deletion of an endogenous gene.

28. The method of claim 26, wherein the aptamer is either a protein aptamer or a nucleic acid aptamer.

29. The method of claim 26, wherein the aptamer performs a function selected from the group consisting of inhibiting expression of a gene, increasing expression of a gene, inhibiting protein-protein interactions, enhancing protein-protein interactions, inhibiting an activity of a protein, and enhancing an activity of a protein.

30. The method of claim 26, wherein the protein-protein interaction detection system is selected from the group consisting of a yeast two-hybrid system, a Ras recruitment system, a split ubiquitin system, and a protein fragment complementation systems.

31. The method of claim 26, wherein the heterologous gene is a human gene.

32. The method of claim 31, wherein the human gene comprises a set of alleles, each differing by one or more SNPs (small nucleotide polymorphisms).

33. The method of claim 18, wherein robotic manipulation is utilized.

34. The method of claim 18, wherein the resulting haploid yeast strain comprises a genetic tag.

35. The method of claim 34, wherein the genetic tag is a 20 mer oligonucleotide sequence.

36. A method for conducting synthetic lethal analysis of yeast colonies within an output array of multiple diploid yeast strains, the method comprising:
   a) generating an output array of multiple resulting diploid yeast strains according to the method of claim 1;
   b) comparing growth and viability of the resulting diploid yeast strains arrayed in step d) of claim 1 to growth and viability of the derivative yeast strains mated in step b) of claim 1;
   c) detecting which resulting diploid strains contain synthetic lethal resulting genetic alterations by observing differences in the growth and viability of the resulting diploid yeast strains as compared to the growth and viability of the derivative yeast strains.

* * * * *